US010642156B2

(12) United States Patent
Toida et al.

(10) Patent No.: US 10,642,156 B2
(45) Date of Patent: *May 5, 2020

(54) RESIST BASE MATERIAL, RESIST COMPOSITION AND METHOD FOR FORMING RESIST PATTERN

(71) Applicant: Mitsubishi Gas Chemical Company, Inc., Tokyo (JP)

(72) Inventors: Takumi Toida, Kanagawa (JP); Masatoshi Echigo, Tokyo (JP); Takashi Sato, Kanagawa (JP); Youko Shimizu, Kanagawa (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 15 days.

This patent is subject to a terminal disclaimer.

(21) Appl. No.: 15/562,841

(22) PCT Filed: Mar. 17, 2016

(86) PCT No.: PCT/JP2016/058519
§ 371 (c)(1),
(2) Date: Sep. 28, 2017

(87) PCT Pub. No.: WO2016/158458
PCT Pub. Date: Oct. 6, 2016

(65) Prior Publication Data
US 2018/0107113 A1    Apr. 19, 2018

(30) Foreign Application Priority Data

Mar. 30, 2015   (JP) .................. 2015-069991

(51) Int. Cl.
| | |
|---|---|
| *G03F 7/038* | (2006.01) |
| *G03F 7/004* | (2006.01) |
| *C08G 83/00* | (2006.01) |
| *C08L 61/12* | (2006.01) |
| *C07C 39/15* | (2006.01) |
| *C08G 8/04* | (2006.01) |
| *C08G 8/20* | (2006.01) |
| *G03F 7/16* | (2006.01) |
| *G03F 7/20* | (2006.01) |
| *G03F 7/30* | (2006.01) |

(52) U.S. Cl.
CPC ............. *G03F 7/038* (2013.01); *C07C 39/15* (2013.01); *C08G 8/04* (2013.01); *C08G 8/20* (2013.01); *C08G 83/00* (2013.01); *C08L 61/12* (2013.01); *G03F 7/004* (2013.01); *C07C 2601/16* (2017.05); *G03F 7/16* (2013.01); *G03F 7/20* (2013.01); *G03F 7/30* (2013.01)

(58) Field of Classification Search
CPC ... G03F 7/038; G03F 7/30; G03F 7/20; G03F 7/16; C08L 61/12; C07C 39/15; C07C 2601/16; C08G 8/04; C08G 8/20; C08G 83/00

See application file for complete search history.

(56) References Cited

U.S. PATENT DOCUMENTS

| | | |
|---|---|---|
| 3,702,245 A | 11/1972 | Simon |
| 4,115,128 A | 9/1978 | Kita |
| 4,670,495 A | 6/1987 | Evans |
| 5,173,389 A | 12/1992 | Uenishi |
| 5,281,689 A | 1/1994 | Bendier |
| 5,376,498 A | 12/1994 | Kajita et al. |
| 5,565,300 A | 10/1996 | Uenishi |
| 9,372,404 B2 | 6/2016 | Watanabe |
| 2002/0156189 A1 | 10/2002 | Ogura |
| 2004/0254327 A1 | 12/2004 | Boyles |
| 2005/0255712 A1 | 11/2005 | Kato |
| 2007/0059632 A1 | 3/2007 | Oguro |
| 2008/0044757 A1 | 2/2008 | De Silva |
| 2008/0113294 A1 | 5/2008 | Echigo |
| 2008/0153031 A1 | 6/2008 | Echigo et al. |
| 2009/0081582 A1 | 3/2009 | Hattori |
| 2010/0316950 A1 | 12/2010 | Oguro |
| 2011/0177459 A1 | 7/2011 | Ogihara |
| 2012/0064725 A1 | 3/2012 | Kinsho |
| 2012/0171611 A1 | 7/2012 | Ideno |
| 2013/0302990 A1 | 11/2013 | Watanabe |
| 2014/0065533 A1 | 3/2014 | Wu |
| 2014/0186776 A1 | 7/2014 | Uchiyama |
| 2014/0224765 A1 | 8/2014 | Minegishi |
| 2014/0248561 A1 | 9/2014 | Echigo |
| 2014/0308615 A1 | 10/2014 | Echigo et al. |
| 2014/0349222 A1 | 11/2014 | Shibui |

(Continued)

FOREIGN PATENT DOCUMENTS

| | | |
|---|---|---|
| CN | 101889247 A | 11/2010 |
| CN | 103304385 A | 9/2013 |

(Continued)

OTHER PUBLICATIONS

Mora et al "Interface Engineering of Synthetic Pores: Towards Hypersensitive Biosensors", Chem. Eur. J. 1008, vol. 14, pp. 1947-1953 (Year: 2008).*

Jang et. al, Synthesis and Supramolecular Nanostructure of Amphiphilic Rigid Aromatic-Flexible Dendritic Block Molecules, Chemistry of Materials, 2004, vol. 16, p. 4226-4231. (Year: 2004).*

Arai, Tadashi; Hattori, Takashi; Shiraishi, Hiroshi; Fukuda, Hiroshi, Polyphenol-Based Positive-Tone EB Resist—Resist Shade Mask, Journal of Photopolymer Science and Technology, 2004, 17(4), 567-573.

Boyles, David A. et al., "Synthesis of High Aspect Ratio Bisphenols and Polycarbonates Incorporating Bisaryl Units", Macromolecules, 2005, 38 (9), pp. 3622-3629, DOI: 10.1021/ma048616m Publication Date (Web): Mar. 30, 2005.

(Continued)

*Primary Examiner* — Cynthia Hamilton
(74) *Attorney, Agent, or Firm* — Fitch, Even, Tabin & Flannery LLP

(57) ABSTRACT

The present invention provides a resist base material containing a compound having a specific structure and/or a resin derived from the compound as a monomer.

14 Claims, No Drawings

(56) References Cited

U.S. PATENT DOCUMENTS

| | | |
|---|---|---|
| 2015/0037735 A1 | 2/2015 | Yang |
| 2015/0212418 A1 | 7/2015 | Nishimaki |
| 2016/0068709 A1 | 3/2016 | Endo |
| 2017/0073288 A1 | 3/2017 | Makinoshima et al. |
| 2017/0075220 A1 | 3/2017 | Sato et al. |
| 2017/0349564 A1 | 12/2017 | Toida |
| 2018/0029968 A1 | 2/2018 | Toida |
| 2018/0044270 A1 | 2/2018 | Horiuchi |
| 2018/0081270 A1 | 3/2018 | Echigo |
| 2018/0095368 A1* | 4/2018 | Toida ............... C07C 37/72 |
| 2018/0107113 A1 | 4/2018 | Toida |

FOREIGN PATENT DOCUMENTS

| | | |
|---|---|---|
| CN | 103804196 A | 5/2014 |
| CN | 104557552 A | 4/2015 |
| DE | 1167854 B | 4/1964 |
| EP | 0395049 A1 | 10/1990 |
| EP | 0440238 A2 | 8/1991 |
| EP | 0604056 A2 | 6/1994 |
| EP | 2660257 A1 | 11/2013 |
| EP | 2743770 A1 | 6/2014 |
| EP | 3118183 A1 | 1/2017 |
| EP | 3118684 A1 | 1/2017 |
| JP | S54037492 B2 | 11/1979 |
| JP | H02285351 A | 11/1990 |
| JP | H03228057 A | 10/1991 |
| JP | H04297430 A | 10/1992 |
| JP | H05019463 A | 1/1993 |
| JP | H05067701 A | 3/1993 |
| JP | H06242601 A | 9/1994 |
| JP | H07271037 A | 10/1995 |
| JP | H08137100 A | 5/1996 |
| JP | H09106070 A | 4/1997 |
| JP | H10161332 A | 6/1998 |
| JP | H10307384 A | 11/1998 |
| JP | 2001122828 A | 5/2001 |
| JP | 2002275112 A | 9/2002 |
| JP | 2002334869 A | 11/2002 |
| JP | 2004177668 A | 6/2004 |
| JP | 2004271838 A | 9/2004 |
| JP | 2005187335 A | 7/2005 |
| JP | 2005250434 A | 9/2005 |
| JP | 2005266741 A | 9/2005 |
| JP | 2005-326838 A | 11/2005 |
| JP | 2006259482 A | 9/2006 |
| JP | 2006276742 A | 10/2006 |
| JP | 2007204574 A | 8/2007 |
| JP | 2007226170 A | 9/2007 |
| JP | 2007226204 A | 9/2007 |
| JP | 2007241271 A | 9/2007 |
| JP | 2008-145539 A | 6/2008 |
| JP | 2009080203 A | 4/2009 |
| JP | 2009-098155 A | 5/2009 |
| JP | 2009-173623 A | 8/2009 |
| JP | 2010077038 A | 4/2010 |
| JP | 2012077295 A | 4/2012 |
| JP | 2012083731 A | 4/2012 |
| SG | 11201607443X | 10/2016 |
| SG | 11201607444V | 10/2016 |
| WO | 2004037879 A2 | 5/2004 |
| WO | 2004066377 A1 | 8/2004 |
| WO | 2005101127 A1 | 10/2005 |
| WO | 2009072465 A1 | 6/2009 |
| WO | 2011034062 A1 | 3/2011 |
| WO | 2012/153991 A2 | 11/2012 |
| WO | 2012165507 A1 | 12/2012 |
| WO | 2013/024777 A1 | 2/2013 |
| WO | 2013036546 A2 | 3/2013 |
| WO | 2013134997 A1 | 9/2013 |
| WO | 2014024836 A1 | 2/2014 |
| WO | 2015/137485 A1 | 9/2015 |
| WO | 2015/137486 A1 | 9/2015 |
| WO | 2016129679 A1 | 8/2016 |
| WO | 2016158456 A1 | 10/2016 |
| WO | 2016163456 A1 | 10/2016 |
| WO | 2017038979 A1 | 3/2017 |
| WO | 2017043561 A1 | 3/2017 |

OTHER PUBLICATIONS

Cammack, R., et al., Oxford Dictionary of Biochemistry and Molecular Biology (2nd Edition). Oxford University Press, (2006), pp. 419, 422.

Cantin, Katy, et al. "Studies Toward the Synthesis of Phenylacetylene Macrocycle Based Rotaxane Precursors as Building Blocks for Organic Nanotubes," European Journal of Organic Chemistry, 2012, pp. 5335-5349.

Chaumont, Clement, et al., "Synthesis, topology and energy analysis of crystaline resorcinol-based oligophenylene molecules with various symmetries," CrystEngComm, vol. 15, No. 34, Jan. 2013, pp. 6845-6862.

Chen, Huanqing, et al., "Biphen[n]arenes," Chemical Science; vol. 6, No. 197; The Royal Society of Chemistry; 2015; pp. 197-202.

De Silva, Anuja; Forman, Drew; Ober, Christopher K., Molecular Glass Resists for EUV Lithography, Proceedings of SPIE—The International Society for Optical Engineering (Pt. 2, Advances in Resist Technology and Processing XXIII), 2006, 6153, 615341/1-615341/10.

Hardinger, Steven A., "Methine Group", Illustrated Glossary of Organic Chemistry, Department of Chemistry & Biochemistry, UCLA, copyright 2010-2017, 2 pages downloaded Feb. 16, 2018.

Ihori, Yoichi, et al., "Chiral Zirconium Catalysts Using Multidentate BINOL Derivatives for Catalytic Enantioselective Mannich-Type Reactions; Ligand Optimization and Approaches to Elucidation of the Catalyst Structure," Journal of the American Chemical Society, 2005, vol. 127, No. 44, pp. 15528-15535.

James, "9 Nomenclature Conventions to Know", Master Organic Chemistry, copyright 2018, 26 pages downloaded Feb. 15, 2018.

Lin, Ying, et al., "Palladium-Catalyzed [3+2] Cycloaddition Reaction of (Diarylmethylene)-cyclopropa[b]naphthalenes with Arynes: An Efficient Synthesis of 11-(Diarylmethylene)-11H-benzo[b]fluorenes," European Journal of Organic Chemistry, vol. 2011, No. 16, Jan. 2011, pp. 2993-3000.

Pegenau, Annegret, et al., "The Importance of Micro Segregation for Mesophase Formation: Thermotropic Columnar Mesophases of Tetrahedral and other Low-Aspect-Ratio Organic Materials," Chem. Eur. J., vol. 5, No. 5, May 1999, pp. 1643-1660.

Rathore, Rajendra, Burns, Carrie L., and Deselnicu, Mihaela I., "Multiple-Electron Transfer in a Single Step. Design and Synthesis of Highly Charged Cation-Radical Salts," Organic Letters, Sep. 1, 2001, vol. 3, No. 18, pp. 2887-2890.

Reddy, D. Shekhar, et al., Charge-Transfer diamondoid lattices: An Unprecedentedly Huge and Highly Catenating Diamondoid Network Arising from a Tetraphenol as a Tetrahedral Node and Benzoquinone as a Linear Spacer, Angewandte Chemie, International Edition, 2000, 39(23), pp. 4266-268, scheme 1, compound 1.

Ryu, Ja-Hyoung, et al.," Self-Assembling Molecular Dumbbells: From Nanohelices to Nanocapsules Triggered by Guest Intercalation," Angewandte Chemie International Edition, vol. 45, No. 32, 2006, pp. 5304-5307.

Schultz, Andreas, et al., Tetraphenylethene-Derived Columnar Liquid Crystals and Their Oxidative Photocyclization, European Journal of Organic Chemistry, 2003, (15), pp. 2829-2839, p. 2832, Scheme 4, Compound 17.

Sundberg, Linda K.; Wallraff, Gregory M.; Friz, Alexander M.; Davis, Blake W.; Swanson, Sally A.; Brock, Phillip J.; Rettner, Charles T.; Hinsberg, William D., Visualization of the Develop Process, Proceedings of SPIE (Advances in Resist Materials and Processing Technology XXVIII), 2011, 7972, 797201/1-797201/10.

Vogl, Erasmus M. et al., Linking BINOL: C2-Symmetric Ligands for Investigations on Asymmetric Catalysis, Tetrahedron Letters, 1998, 39(43), pp. 7917-7920, pp. 7918 to 7919, compounds 2, 9.

Yamada, Arisa, et al.; Development of High Resolution Molecular Resist Based on Tris((hydroxypheny)pheny)benzene; Journal of Photopolymer Science and Technology; vol. 23, No. 1; 2010; pp. 91-95.

(56) References Cited

OTHER PUBLICATIONS

International Search Report on Patentability for PCT/JP2016/058519 dated Jun. 14, 2016; English translation submitted herewith (5 pages).
Toru Amaya, Akihiro Miyasaka, Toshikazu Hirao, Synthesis of three-dimensionally arranged bis-biphenol ligand on hexaarylbenzene scaffold and its application for cross-pinacol coupling reaction, Tetrahedron Letters, Jul. 2, 2011, vol. 52, p. 4567-4569.
Cheong-Jin Jang, Ja-Hyoung Ryu, Joon-Dong Lee, Deawon Sohn, and Myongsoo Lee, and Supramolecular Nanostructure of Amphiphilic Rigid Aromatic-Flexible Dendritic Block Molecules, Chemistry of Materials, Sep. 10, 2004, vol. 16, p. 4226-4231.
Bereket Ghebremariam and Stefan Matile, Synthesis of Asymmetric Septi-(p-Phenylene)s, Tetrahedron Letters, May 13, 1998, vol. 39, p. 5335-5338.
T.Nakayama, M.Nomura, K.Haga, M.Ueda: Bull. Chem. Soc. Jpn., 71, 2979(1998).

* cited by examiner

RESIST BASE MATERIAL, RESIST COMPOSITION AND METHOD FOR FORMING RESIST PATTERN

CROSS-REFERENCE TO RELATED APPLICATIONS

This application is a U.S. national phase application filed under 35 U.S.C. § 371 of International Application PCT/JP2016/058519, filed on Mar. 17, 2016, designating the United States, which claims priority from Japanese Application Number 2015-069991, filed Mar. 30, 2015.

FIELD OF THE INVENTION

The present invention relates to a resist base material containing a compound having a specific structure and/or a resin. The present invention also relates to a resist composition containing the base material, and a method for forming a resist pattern using the composition.

BACKGROUND OF THE INVENTION

Polymer based materials capable of forming amorphous thin films have been used so far as typical resist materials. For example, a line pattern of about 45 to 100 nm is formed by irradiating a resist thin film made by coating a substrate with a solution of a polymer resist material such as polymethyl methacrylate, polyhydroxy styrene with an acid dissociation reactive group, or polyalkyl methacrylate with ultraviolet, far ultraviolet, electron beam, extreme ultraviolet (EUV), and X-ray or the like.

However, because polymer based resists have a molecular weight as large as about 10,000 to 100,000 and also wide molecular weight distribution, in lithography using a polymer based resist, roughness occurs on a fine pattern surface; the pattern dimension becomes difficult to be controlled; and so the yield decreases. Therefore, there is a limitation in miniaturization with lithography using a conventional polymer based resist material. In order to make a finer pattern, various low molecular weight resist materials have been proposed so far.

For example, an alkaline development type negative type radiation-sensitive composition (see Patent Documents 1 and 2) using a low molecular weight polynuclear polyphenolic compound as a main component has been suggested.

Also, as a low molecular weight resist material having high heat resistance, an alkaline development type negative type radiation-sensitive composition (see Patent Document 3 and Non Patent Document 1) using a low molecular weight cyclic polyphenolic compound as a main component has been suggested.

LIST OF PRIOR ART DOCUMENTS

Patent Document

Patent Document 1: Japanese Patent Application Laid-Open No. 2005-326838

Patent Document 2: Japanese Patent Application Laid-Open No. 2008-145539

Patent Document 3: Japanese Patent Application Laid-Open No. 2009-173623

Non Patent Document

Non Patent Document 1: T. Nakayama, M. Nomura, K. Haga, M. Ueda: Bull. Chem. Soc. Jpn., 71, 2979 (1998)

SUMMARY OF INVENTION

However, the alkaline development type negative type radiation-sensitive composition using a low molecular weight polynuclear polyphenolic compound as a main component has the disadvantages that the heat resistance is not sufficient and the shape of the resulting resist pattern becomes poor.

Also, the alkaline development type negative type radiation-sensitive composition using a low molecular weight cyclic polyphenolic compound as a main component has problems such as low solubility in a safe solvent used in a semiconductor production process, low sensitivity, and the poor shape of the resulting resist pattern.

In light of the circumstances described above, an object of the present invention is to provide a resist base material which is excellent in heat resistance, has high solubility in a safe solvent, is excellent in storage stability, enables the formation of a good thin film, and can impart a good shape to a resist pattern, a resist composition containing the base material, and a method for forming a resist pattern using the composition.

The present inventors have, as a result of devoted examinations to solve the above problems, found out that a resist base material containing a compound having a specific structure and/or a resin can solve the above problems, and reached the present invention.

More specifically, the present invention is as follows.

[1] A resist base material comprising a compound represented by the following formula (1) and/or a resin derived from the compound as a monomer:

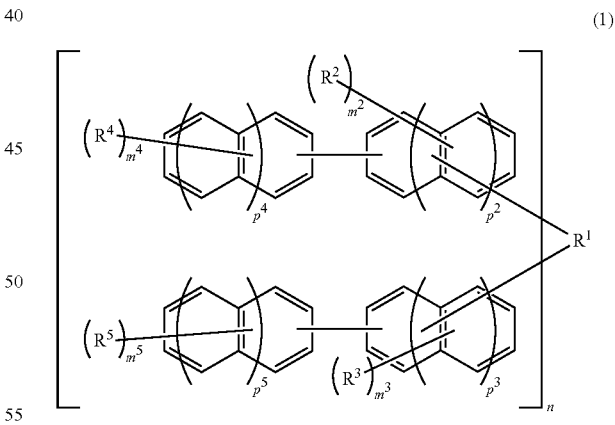

wherein $R^1$ is a 2n-valent group of 1 to 30 carbon atoms; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, or a hydroxyl group, wherein at least one selected from $R^1$ to $R^5$ is a group containing an iodine atom, and at least one of $R^4$ and/or at least one of $R^5$ is one or more kinds selected from a hydroxyl group and a thiol group; $m^2$ and $m^3$ are each independently an integer of 0 to 8; $m^4$ and $m^5$ are each independently an integer of 0 to 9, wherein $m^4$ and $m^5$ are not 0 at the same time; n is an integer of 1 to 4; and $p^2$ to $p^5$ are each independently an integer of 0 to 2.

[2] The resist base material according to [1], wherein at least one of $R^2$ and/or at least one of $R^3$ is one or more kinds selected from a hydroxyl group and a thiol group.

[3] The resist base material according to [1] or [2], wherein the compound represented by the formula (1) is a compound represented by the following formula (1a):

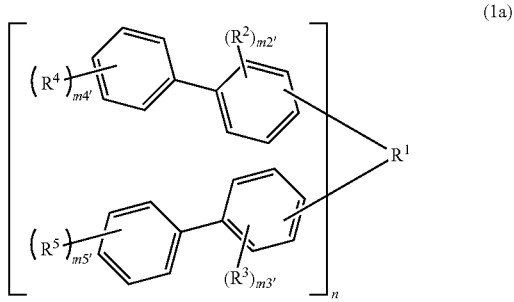

(1a)

wherein $R^1$ to $R^5$ and n are as defined in the description of the above formula (1); $m^{2'}$ and $m^{3'}$ are each independently an integer of 0 to 4; and $m^{4'}$ and $m^{5'}$ are each independently an integer of 0 to 5, wherein $m^{4'}$ and $m^{5'}$ are not 0 at the same time.

[4] The resist base material according to [3], wherein the compound represented by the formula (1a) is a compound represented by the following formula (1b):

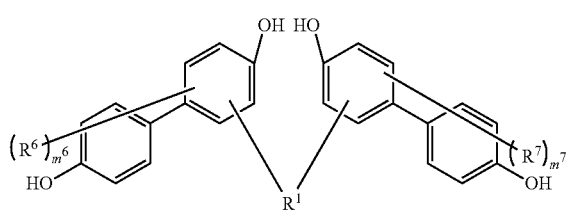

(1b)

wherein $R^1$ is as defined in the description of the above formula (1); $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, or a thiol group, wherein at least one selected from $R^1$, $R^6$, and $R^7$ is a group containing an iodine atom; and $m^6$ and $m^7$ are each independently an integer of 0 to 7.

[5] The resist base material according to [4], wherein the compound represented by the formula (1b) is a compound represented by the following formula (1c):

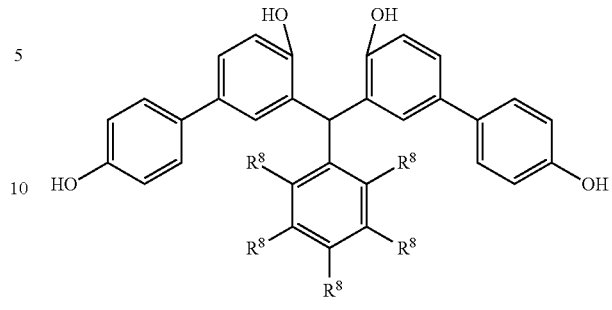

(1c)

wherein $R^8$ are each independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group, wherein at least one of $R^8$ is a group containing an iodine atom.

[6] The resist base material according to [5], wherein the compound represented by the formula (1c) is a compound represented by the following formula (1d):

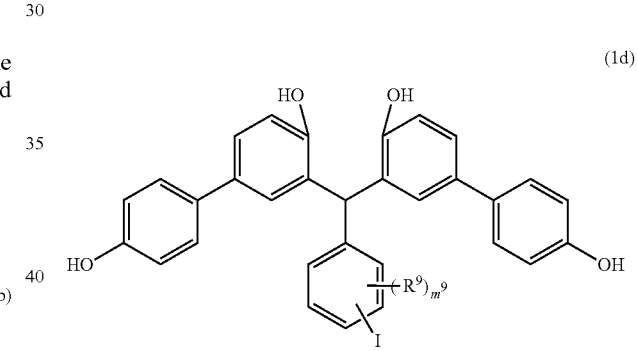

(1d)

wherein $R^9$ are each independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group; and $m^9$ is an integer of 0 to 4.

[7] The resist base material according to any of [1] to [6], wherein the resin is a resin obtained by reacting the compound represented by the formula (1) with a compound having crosslinking reactivity.

[8] The resist base material according to [7], wherein the compound having crosslinking reactivity is an aldehyde, a ketone, a carboxylic acid, a carboxylic acid halide, a halogen-containing compound, an amino compound, an imino compound, an isocyanate, or an unsaturated hydrocarbon group-containing compound.

[9] The resist base material according to [1], wherein the resin has a structure represented by the following formula (2):

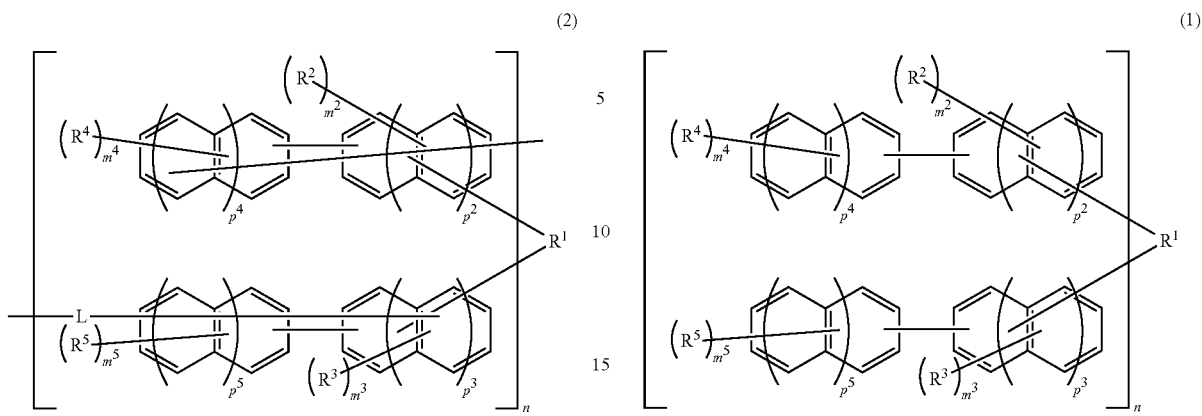

In the above formula (1), $R^1$ is a 2n-valent group of 1 to 30 carbon atoms, and each aromatic ring is bonded via this $R^1$. The 2n-valent group refers to an alkylene group of 1 to 30 carbon atoms (n=1), an alkanetetrayl group of 1 to 30 carbon atoms (n=2), an alkanehexayl group of 2 to 30 carbon atoms (n=3), or an alkaneoctayl group of 3 to 30 carbon atoms (n=4). Examples of the 2n-valent group include ones having a linear hydrocarbon group, a branched hydrocarbon group, or an alicyclic hydrocarbon group. Herein, the alicyclic hydrocarbon group also includes bridged alicyclic hydrocarbon groups. Also, the 2n-valent group may have a double bond, a heteroatom, or an aromatic group of 6 to 30 carbon atoms.

The aromatic group may further have a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group.

$R^2$ to $R^5$ are each independently a monovalent group selected from the group consisting of a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, and a hydroxyl group.

However, at least one selected from $R^1$ to $R^5$ described above is a group containing an iodine atom, and at least one of $R^4$ and/or at least one of $R^5$ is one or more kinds selected from a hydroxyl group and a thiol group.

In the present specification, the "at least one selected from $R^1$ to $R^5$" means "at least one group selected from $R^1$ to $R^5$", and does not mean "at least one kind of group selected from $R^1$ to $R^5$".

$m^2$ and $m^3$ are each independently an integer of 0 to 8, and $m^4$ and $m^5$ are each independently an integer of 0 to 9. However, $m^4$ and $m^5$ are not 0 at the same time.

n is an integer of 1 to 4.

$p^2$ to $p^5$ are each independently an integer of 0 to 2.

As for $R^1$, examples of the group containing an iodine atom include, but not particularly limited to, a linear hydrocarbon group of 1 to 30 carbon atoms substituted with an iodine atom, a branched hydrocarbon group of 3 to 30 carbon atoms substituted with an iodine atom, an alicyclic hydrocarbon group of 3 to 30 carbon atoms substituted with an iodine atom, an aromatic group of 6 to 30 carbon atoms substituted with an iodine atom, and a group having an aromatic group of 6 to 30 carbon atoms substituted with an wherein $R^1$ is a 2n-valent group of 1 to 30 carbon atoms; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, or a hydroxyl group, wherein at least one selected from $R^1$ to $R^5$ is a group containing an iodine atom, and at least one of $R^4$ and/or at least one of $R^5$ is one or more kinds selected from a hydroxyl group and a thiol group; L is a linear or branched alkylene group of 1 to 20 carbon atoms or a single bond; $m^2$ and $m^3$ are each independently an integer of 0 to 8; $m^4$ and $m^5$ are each independently an integer of 0 to 9, wherein $m^4$ and $m^5$ are not 0 at the same time; n is an integer of 1 to 4; and $p^2$ to $p^5$ are each independently an integer of 0 to 2.

[10] A resist composition comprising the resist base material according to any of [1] to [9] and a solvent.

[11] The resist composition according to [10], further comprising an acid generating agent.

[12] The resist composition according to [10] or [11], further comprising an acid crosslinking agent.

[13] A method for forming a resist pattern, comprising the steps of:

coating a substrate with the resist composition according to any of [10] to [12], thereby forming a resist film;

exposing the formed resist film; and developing the exposed resist film.

The present invention can provide a resist base material which is excellent in heat resistance, has high solvent solubility, is excellent in storage stability, enables the formation of a good thin film, and can impart a good shape to a resist pattern.

Mode for Carrying Out Invention

Hereinafter, an embodiment of the present invention will be described. The embodiment below is given in order to illustrate the present invention. The present invention is not limited to only the embodiment.

[Resist Base Material]

The resist base material of the present embodiment contains a compound represented by the following formula (1) and/or a resin derived from the compound as a monomer. By having the following structure, the resist base material of the present embodiment has the advantages that the heat resistance is excellent and the solvent solubility is enhanced.

iodine atom. Among them, a branched hydrocarbon group of 3 to 30 carbon atoms substituted with an iodine atom, an alicyclic hydrocarbon group of 3 to 30 carbon atoms substituted with an iodine atom, an aromatic group of 6 to 30 carbon atoms substituted with an iodine atom, or a group having an aromatic group of 6 to 30 carbon atoms substituted with an iodine atom is preferable, an alicyclic hydrocarbon group of 3 to 30 carbon atoms substituted with an iodine atom, an aromatic group of 6 to 30 carbon atoms substituted with an iodine atom, or a group having an aromatic group of 6 to 30 carbon atoms substituted with an iodine atom is more preferable, and a group having an aromatic group of 6 to 30 carbon atoms substituted with an iodine atom is still more preferable, from the viewpoint of heat resistance.

As for $R^2$ to $R^5$, examples of the group containing an iodine atom include, but not particularly limited to, an iodine atom, a linear aliphatic hydrocarbon group of 1 to 6 carbon atoms substituted with an iodine atom, a branched aliphatic hydrocarbon group of 3 to 6 carbon atoms substituted with an iodine atom, a cyclic aliphatic hydrocarbon group of 3 to 6 carbon atoms substituted with an iodine atom, and an aryl group of 6 carbon atoms substituted with an iodine atom. Among them, an iodine atom, a linear aliphatic hydrocarbon group of 1 to 6 carbon atoms substituted with an iodine atom, or a branched aliphatic hydrocarbon group of 3 to 6 carbon atoms substituted with an iodine atom is preferable, an iodine atom or a linear aliphatic hydrocarbon group of 1 to 6 carbon atoms substituted with an iodine atom is more preferable, and an iodine atom is still more preferable, from the viewpoint of solubility in a safe solvent or the like.

The compound represented by the above formula (1) has high heat resistance attributed to its rigid structure, in spite of its relatively low molecular weight, and may therefore be used even under high temperature baking conditions. Furthermore, the compound represented by the above formula (1) has a relatively low molecular weight and a low viscosity and therefore facilitates uniformly and completely filling even the steps of an uneven substrate (particularly having fine space, hole pattern, etc.).

In the compound represented by the above formula (1), at least one of $R^2$ and/or at least one of $R^3$ is preferably a hydroxyl group and/or a thiol group from the viewpoint of easy crosslinking, further solubility in an organic solvent, and reduction in defect of a coating film.

The compound represented by the above formula (1) is more preferably a compound represented by the following formula (1a) from the viewpoint of the supply of raw materials:

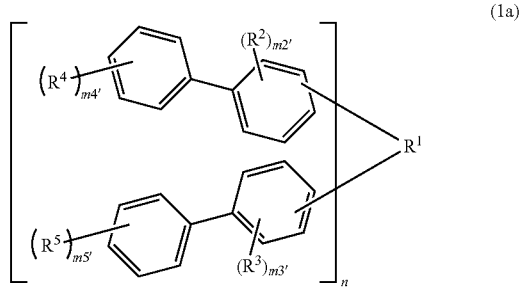

(1a)

In the above formula (1a), $R^1$ to $R^5$ and n are as defined in the description of the above formula (1).

$m^{2'}$ and $m^{3'}$ are each independently an integer of 0 to 4, and $m^{4'}$ and $m^{5'}$ are each independently an integer of 0 to 5. However, $m^{4'}$ and $m^{5'}$ are not 0 at the same time.

The compound represented by the above formula (1a) is still more preferably a compound represented by the following formula (1b) from the viewpoint of solubility in an organic solvent:

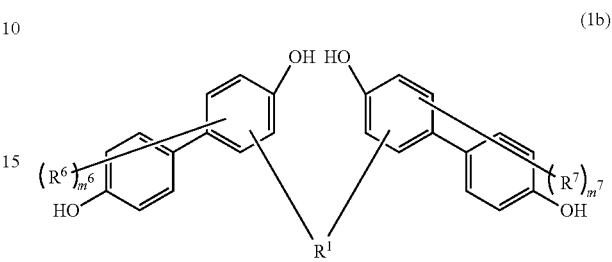

(1b)

In the above formula (1b), $R^1$ is as defined in the description of the above formula (1). $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, a halogen atom, or a thiol group. However, at least one selected from $R^1$, $R^6$, and $R^7$ is a group containing an iodine atom. $m^6$ and $m^7$ are each independently an integer of 0 to 7. In the present specification, the "at least one selected from $R^1$, $R^6$, and $R^{7}$" means "at least one group selected from $R^1$, $R^6$, and $R^{7}$", and does not mean "at least one kind of group selected from $R^1$, $R^6$, and $R^{7}$".

The compound represented by the above formula (1b) is particularly preferably a compound represented by the following formula (1c) from the viewpoint of further solubility in an organic solvent:

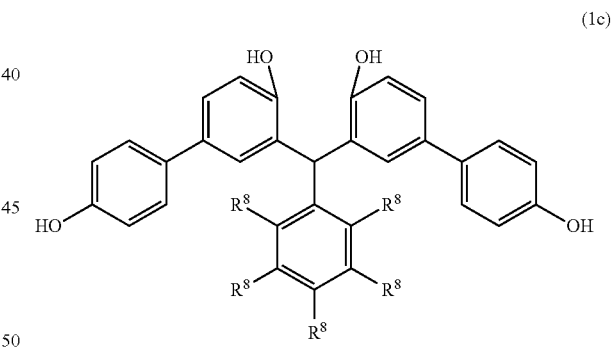

(1c)

In the above formula (1c), $R^8$ are each independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group, wherein at least one of $R^8$ is a group containing an iodine atom, from the viewpoint of quality stabilization.

The compound represented by the above formula (1c) is particularly preferably a compound represented by the following formula (1d) from the viewpoint of easy crosslinking, further solubility in an organic solvent, and reduction in defect of a coating film:

(1d)

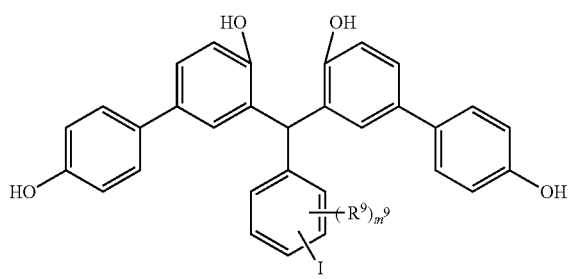

In the formula (1d), $R^9$ are each independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group. $m^9$ is an integer of 0 to 4.

Specific examples of the compound represented by the above formula (1) include, but not limited to, the following compounds:

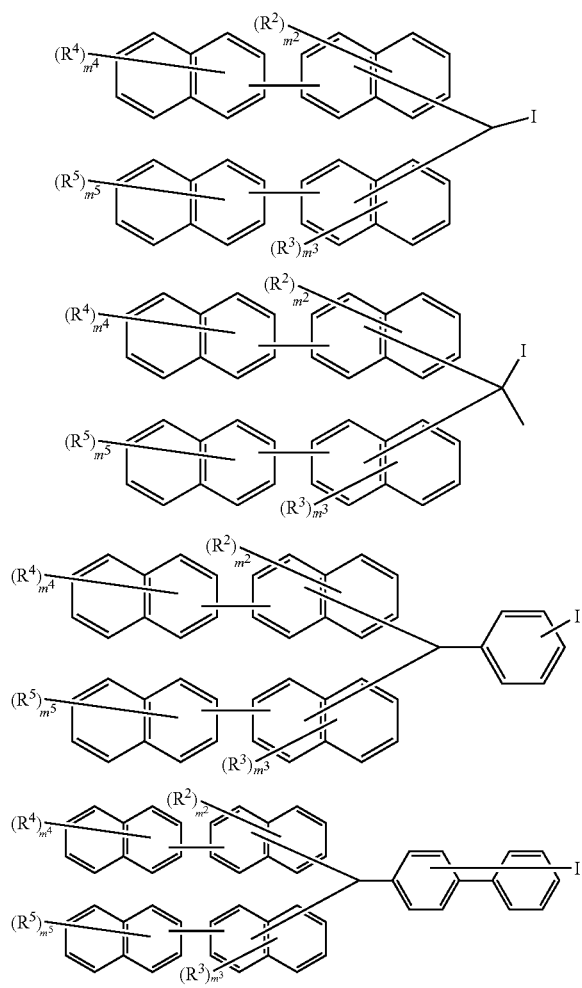

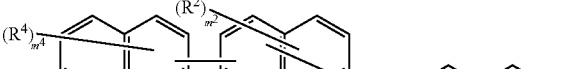
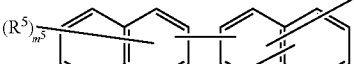
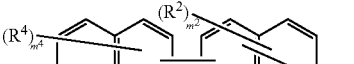
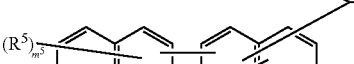
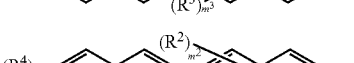
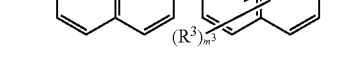
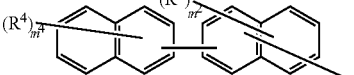
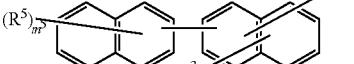
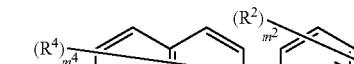
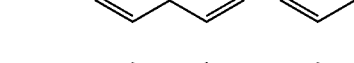
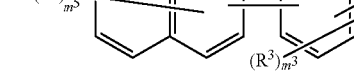
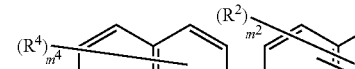
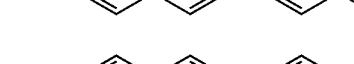
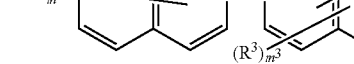
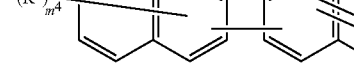
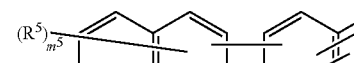

-continued
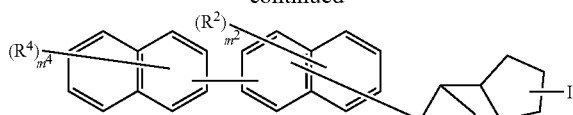
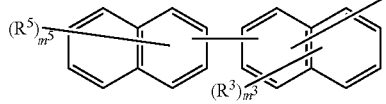
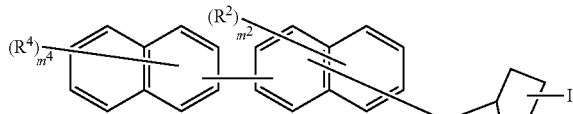
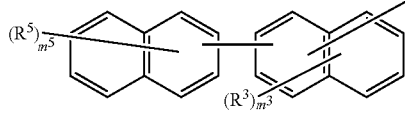
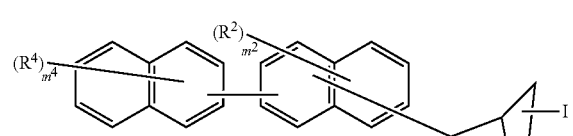
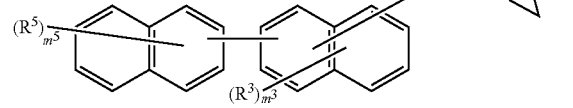
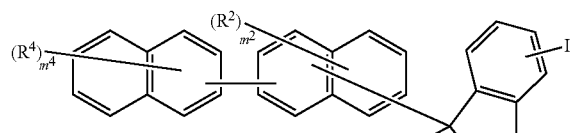
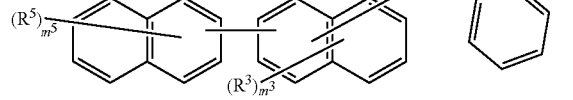
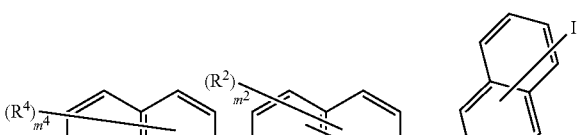
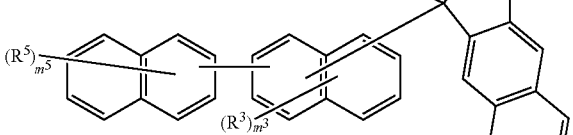
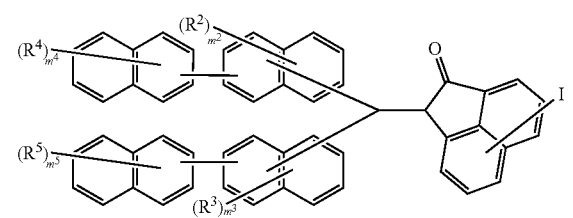
-continued
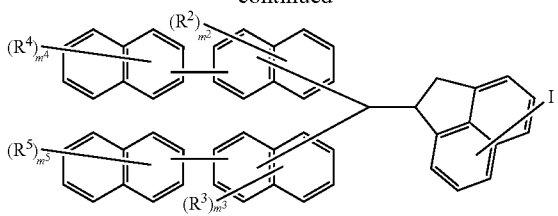
In the above compounds, $R^2$ to $R^5$ and $m^2$ to $m^5$ are as defined in the description of the above formula (1).
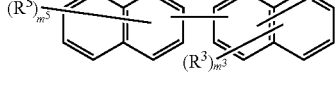
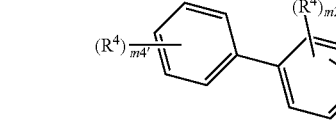
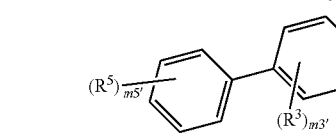
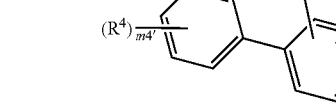
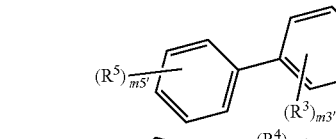
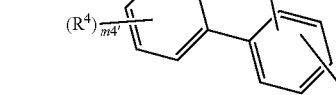
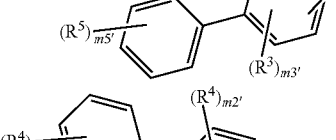
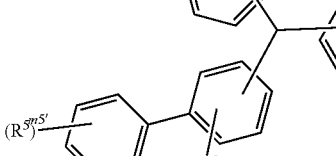
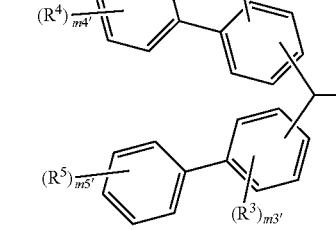

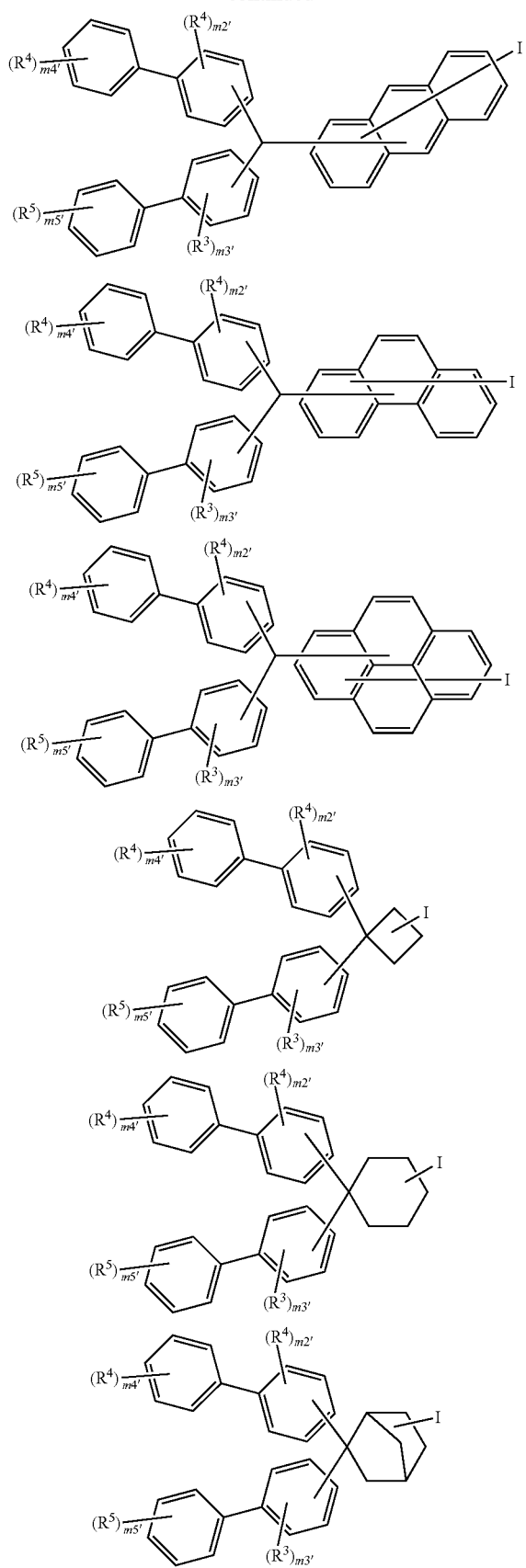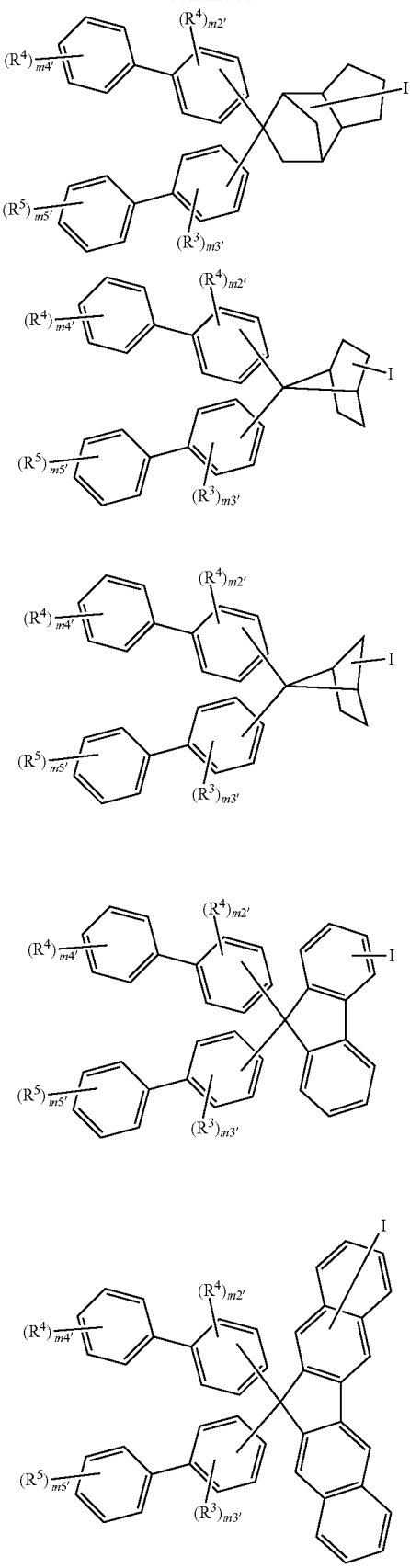

-continued
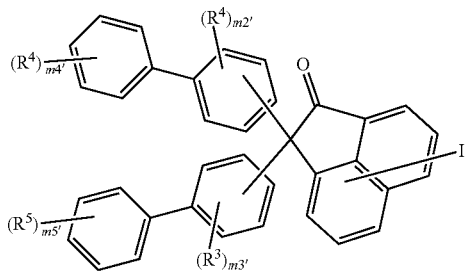
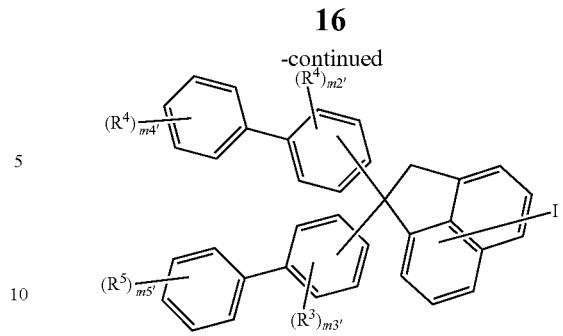
In the above compounds, $R^2$ to $R^5$ are as defined in the description of the above formula (1).
$m^{2'}$ and $m^{3'}$ are each independently an integer of 0 to 4, and $m^{4'}$ and $m^{5'}$ are each independently an integer of 0 to 5. However, $m^{4'}$ and $m^{5'}$ are not 0 at the same time.
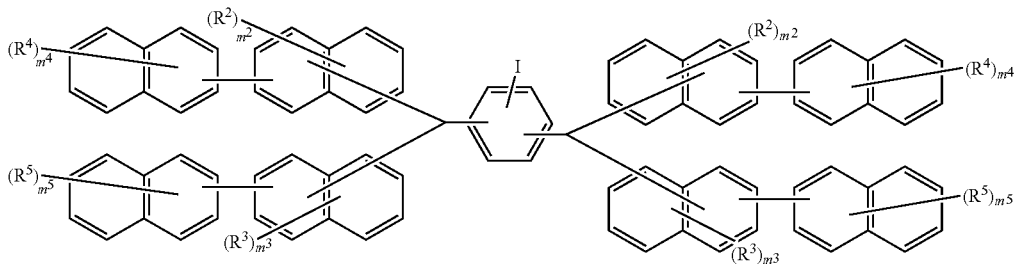
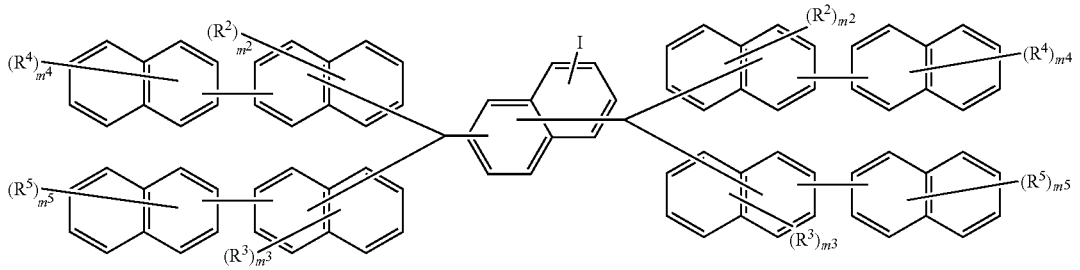
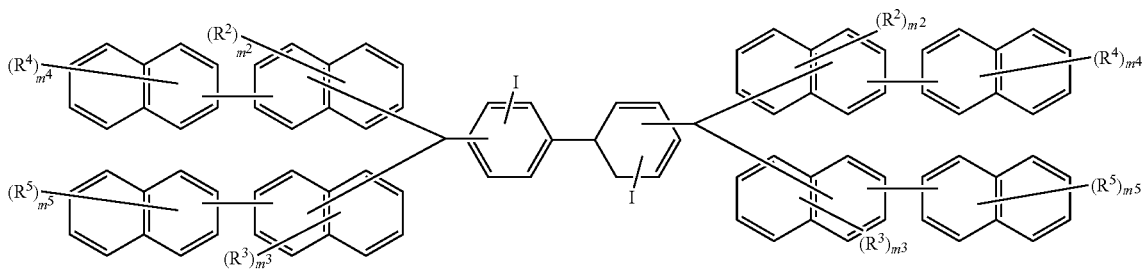
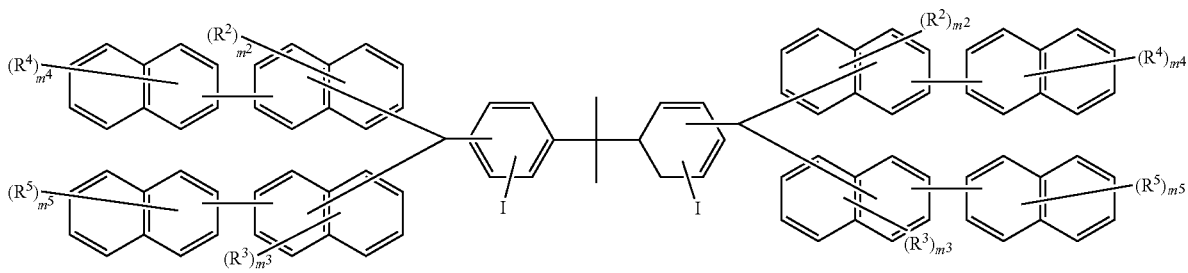

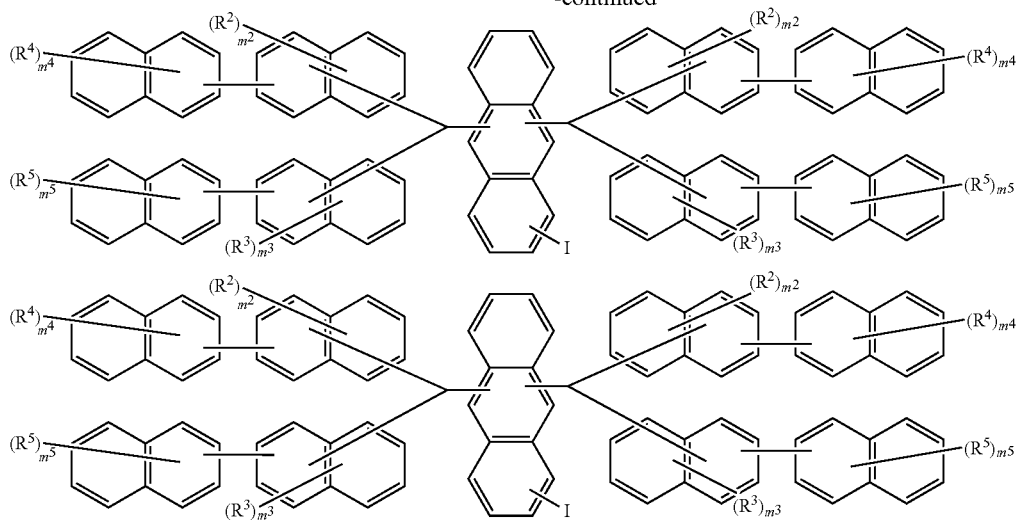
In the above compounds, $R^2$ to $R^5$ and $m^2$ to $m^5$ are as defined in the description of the above formula (1).
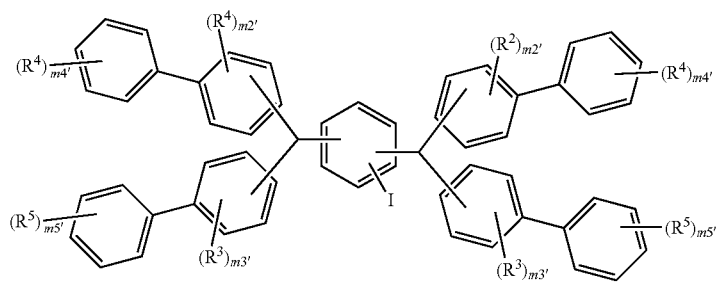
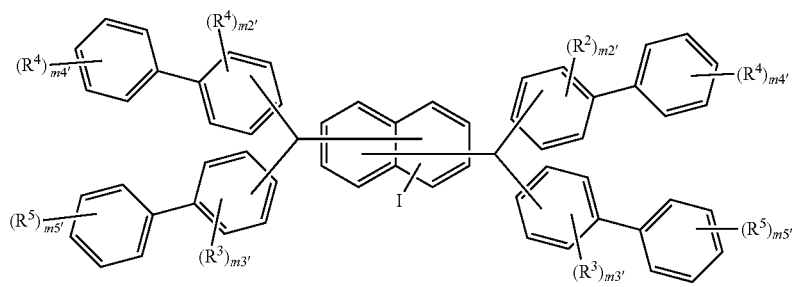
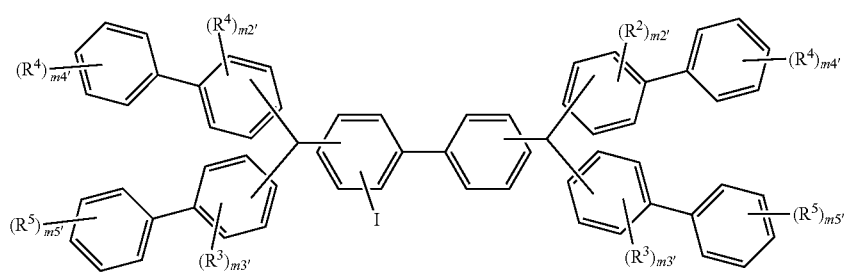

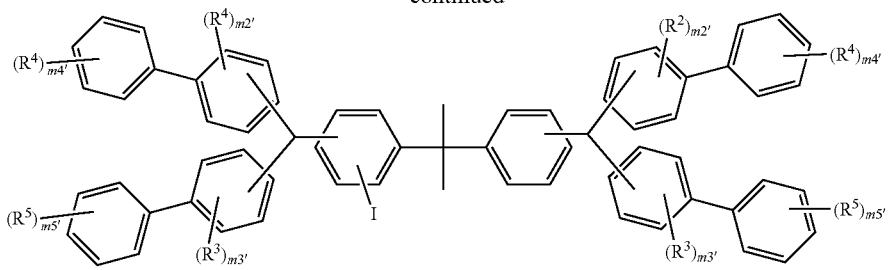
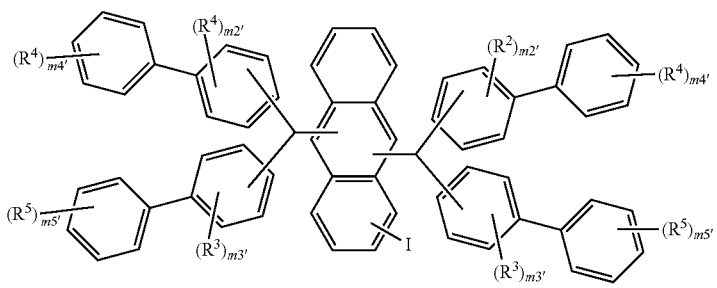
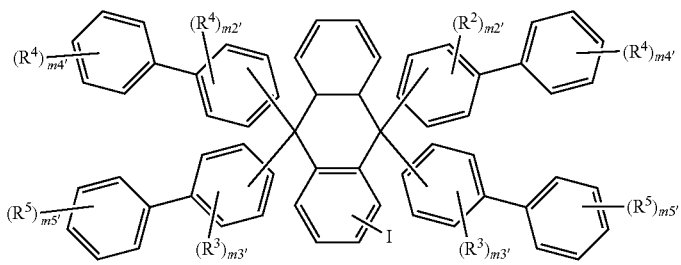
In the above compounds, $R^2$ to $R^5$ are as defined in the description of the above formula (1).
$m^{2'}$ and $m^{3'}$ are each independently an integer of 0 to 4, and $m^{4'}$ and $m^{5'}$ are each independently an integer of 0 to 5. However, $m^{4'}$ and $m^{5'}$ are not 0 at the same time.
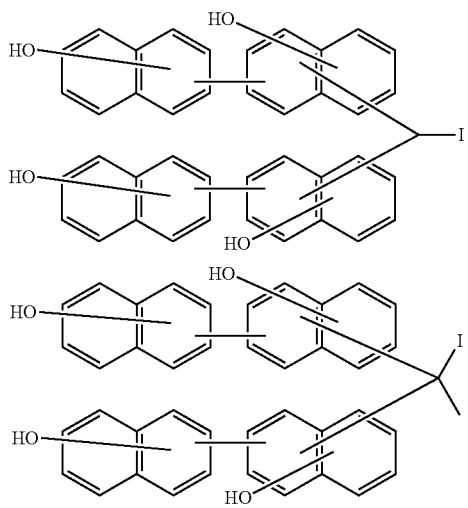

-continued
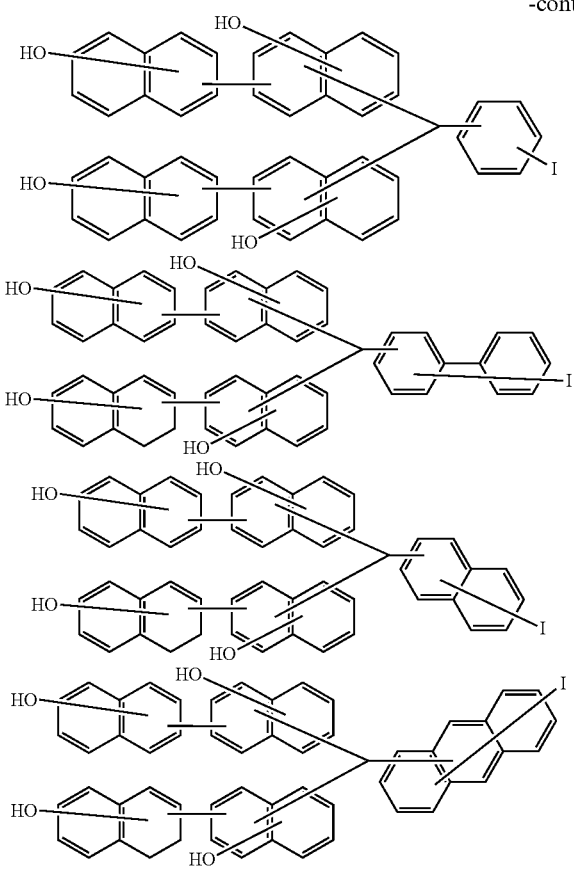
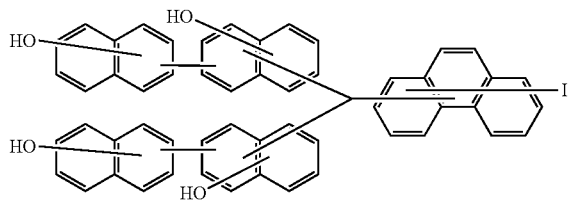
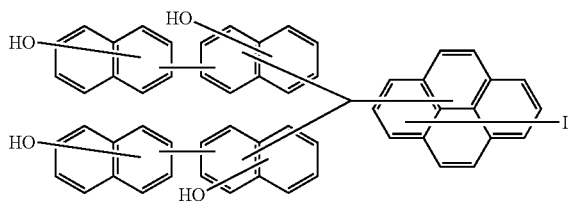
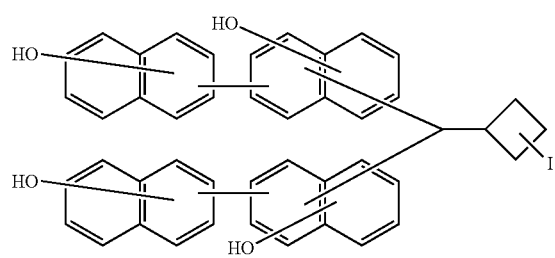

-continued
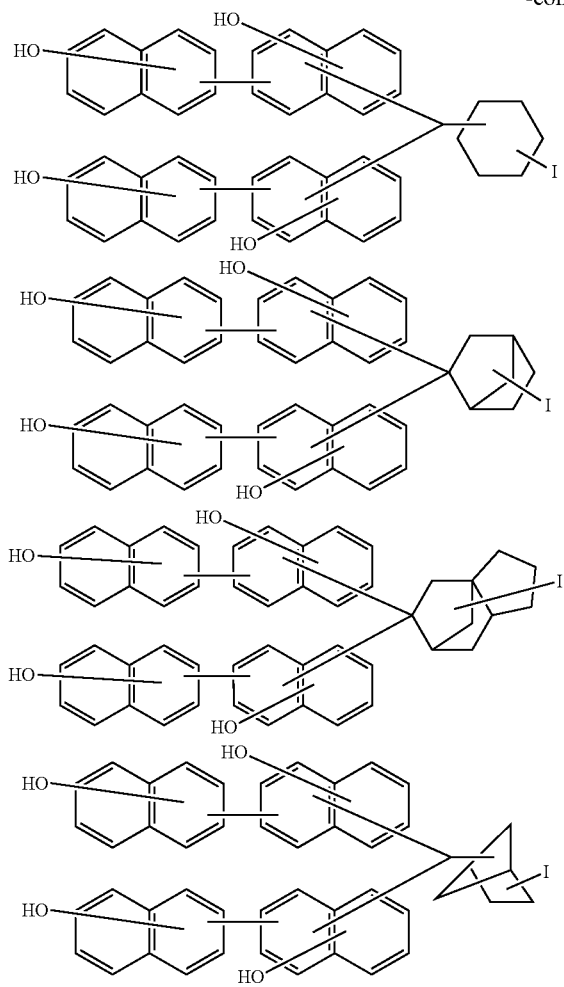
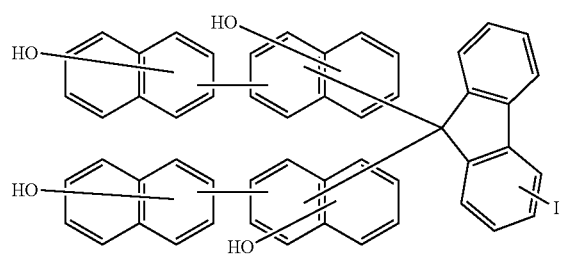
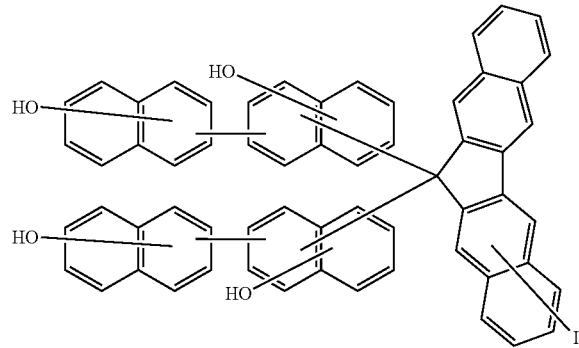

-continued
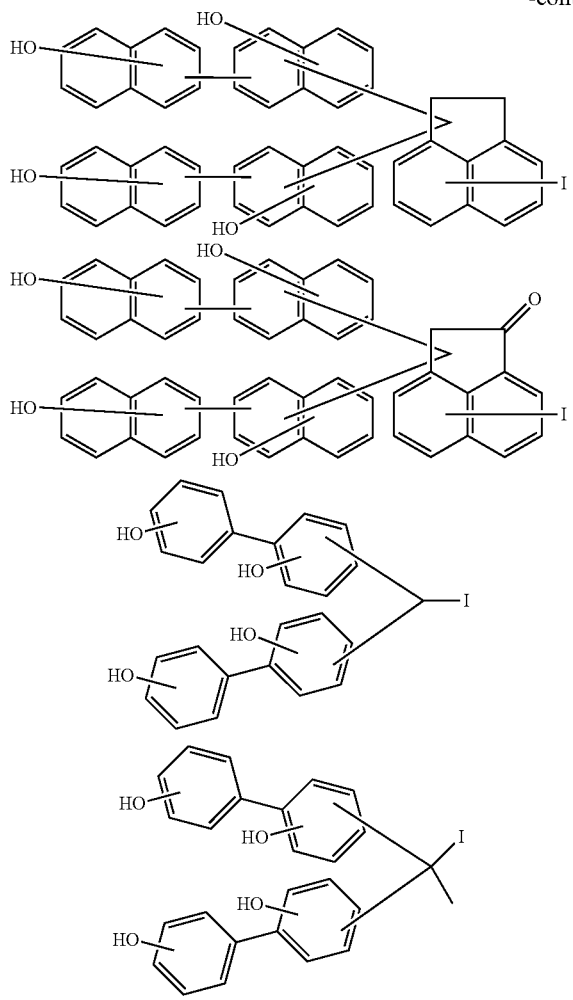
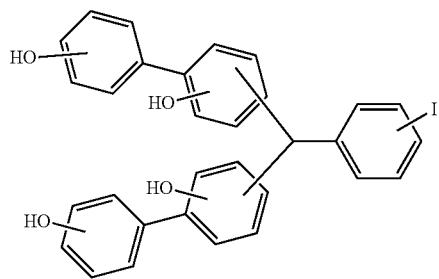
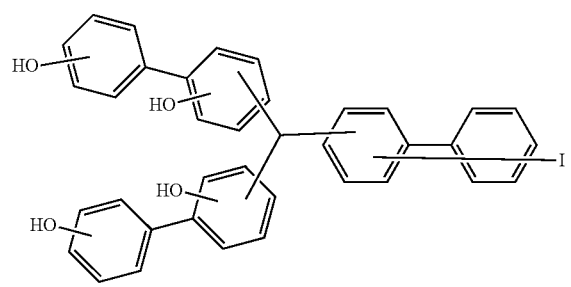

-continued
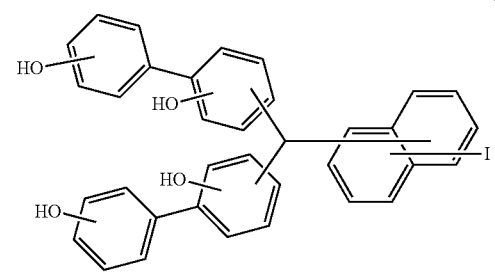
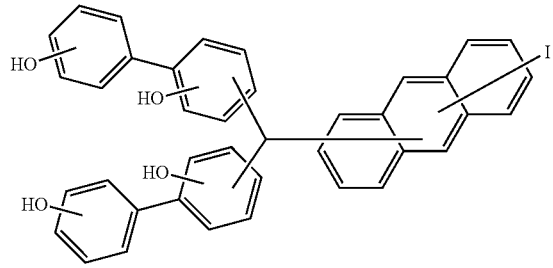
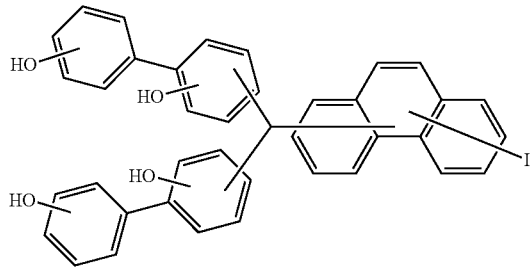
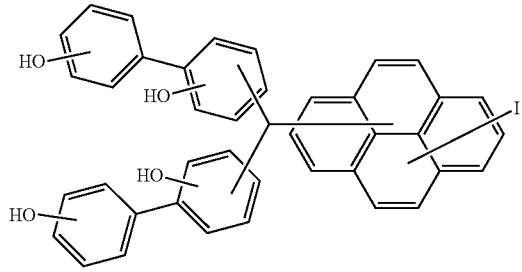
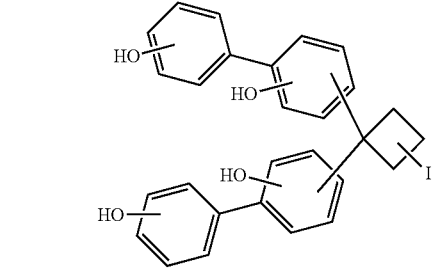
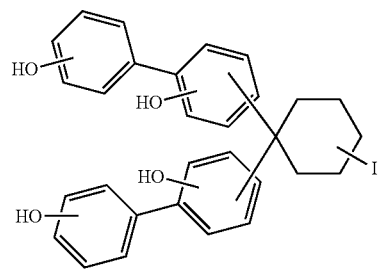

-continued
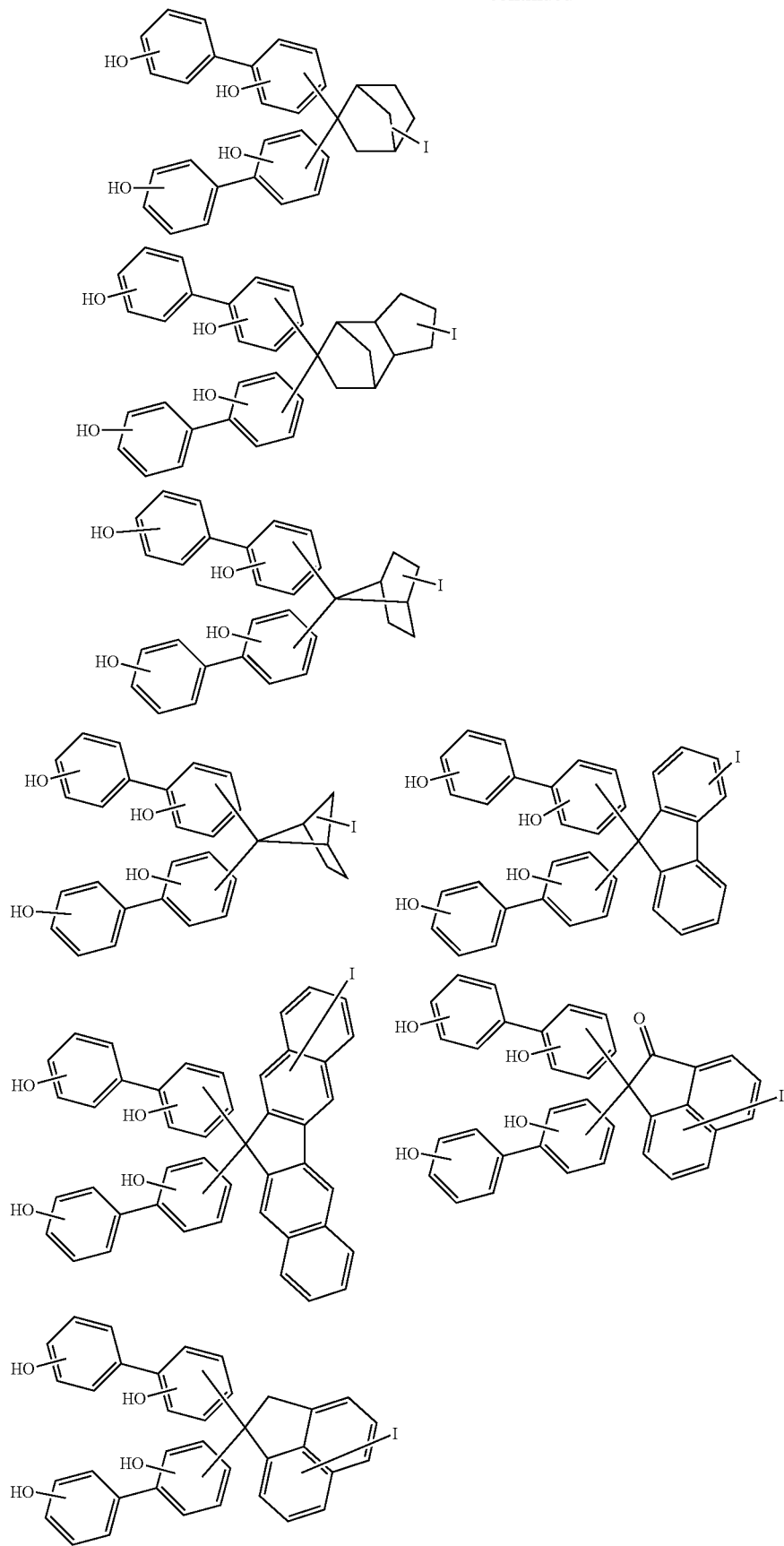

-continued
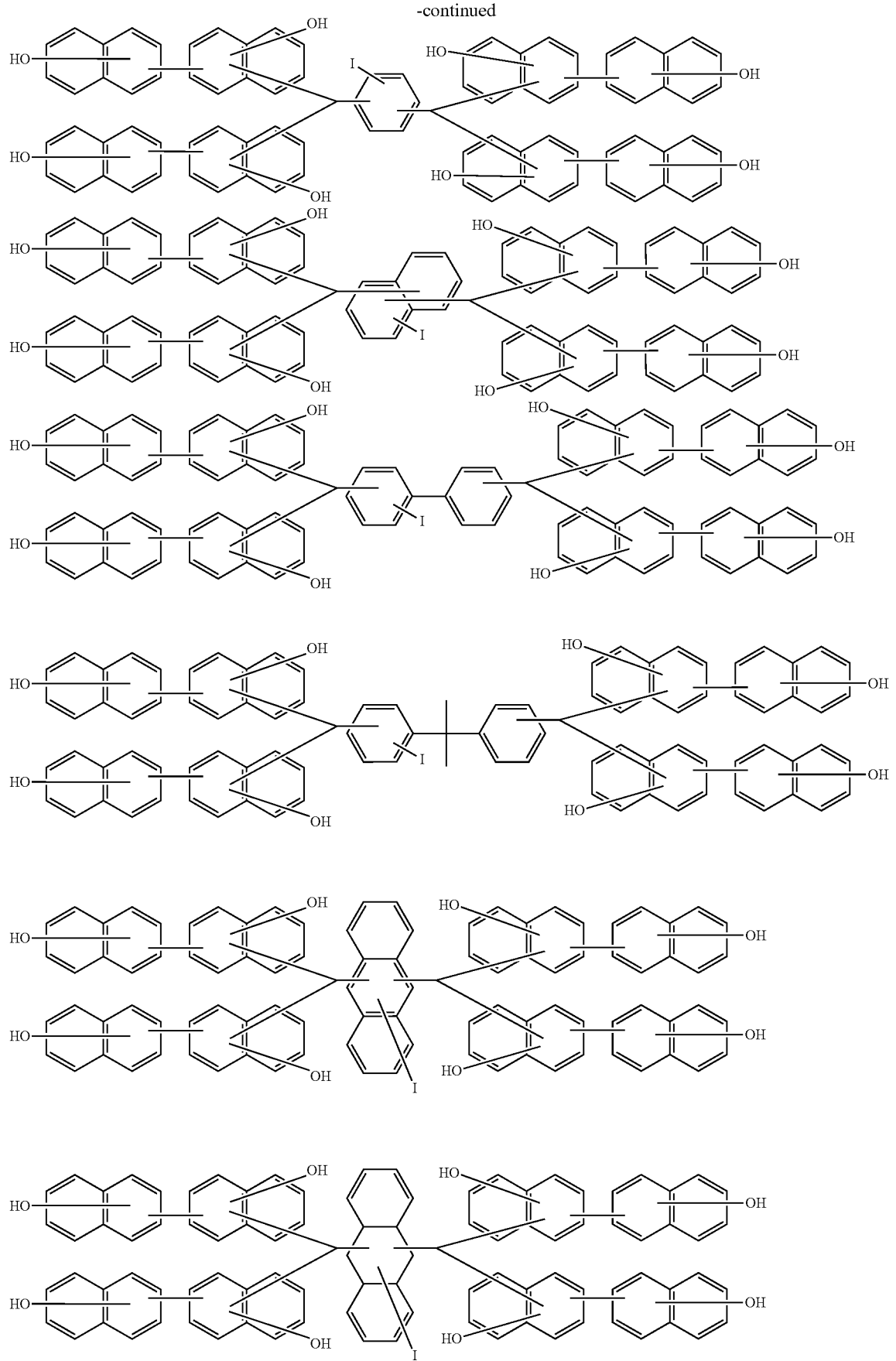

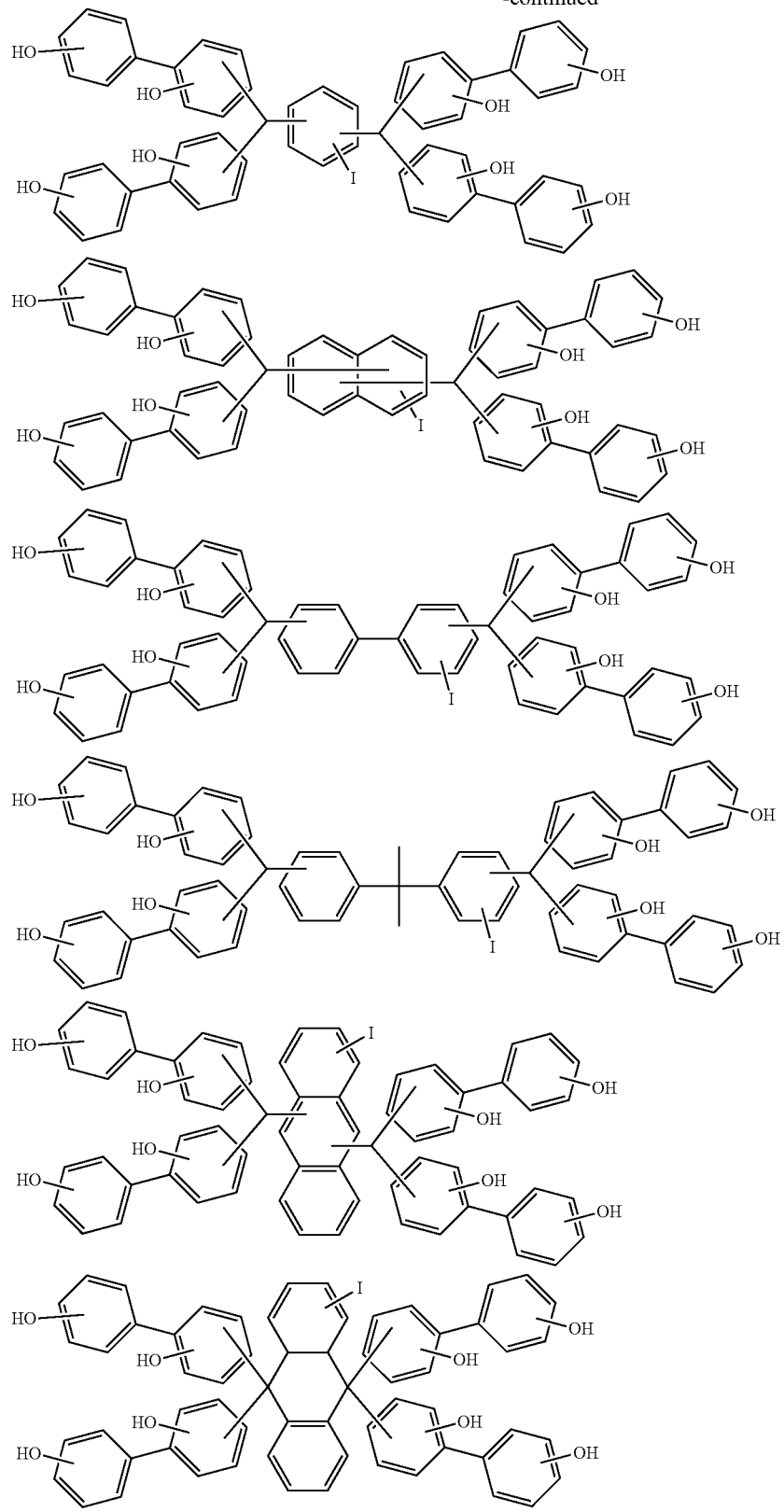
The compound represented by the formula (1) according to the present embodiment can be arbitrarily synthesized using a publicly known approach, and the synthesis approach is not particularly limited. The compound represented by the above formula (1) can be obtained, for example, by subjecting one or more kinds of compounds (A1) selected from the group consisting of a biphenol, a bithiophenol, a binaphthol, a bithionaphthol, or a bianthracenediol, and one or more kinds of compounds (A2) selected from the group consisting of an aldehyde or a ketone to polycondensation reaction in the presence of an acid catalyst at normal pressure. If necessary, this reaction can also be carried out under increased pressure.

Examples of the biphenol include, but not particularly limited to, biphenol, methylbiphenol, and methoxybiphenol. These biphenols may be used alone as one kind or may be used in combination of two or more kinds. Among them, biphenol is more preferable from the viewpoint of the stable supply of raw materials.

Examples of the bithiophenol include, but not particularly limited to, bithiophenol, methylbithiophenol, and methoxybithiophenol. These bithiophenols may be used alone as one kind or may be used in combination of two or more kinds. Among them, bithiophenol is more preferable from the viewpoint of the stable supply of raw materials.

Examples of the binaphthol include, but not particularly limited to, binaphthol, methylbinaphthol, and methoxybinaphthol. These binaphthols may be used alone as one kind or may be used in combination of two or more kinds. Among them, binaphthol is more preferable from the viewpoint of increasing a carbon atom concentration and improving heat resistance.

Examples of the bithionaphthol include, but not particularly limited to, bithionaphthol, methylbithionaphthol, and methoxybithionaphthol. These bithionaphthols may be used alone as one kind or may be used in combination of two or more kinds. Among them, bithionaphthol is more preferably used from the viewpoint of increasing a carbon atom concentration and improving heat resistance.

The aldehyde is preferably a compound of 2 to 59 carbon atoms having 1 to 4 formyl groups and a group containing an iodine atom, and is selected from an aromatic aldehyde compound and an aliphatic aldehyde compound.

The aromatic aldehyde compound is preferably an aldehyde compound of 7 to 24 carbon atoms. Examples thereof include iodobenzaldehyde, methyliodobenzaldehyde, dimethyliodobenzaldehyde, ethyliodobenzaldehyde, propyliodobenzaldehyde, butyliodobenzaldehyde, ethylmethyliodobenzaldehyde, isopropylmethyliodobenzaldehyde, diethyliodobenzaldehyde, methoxyiodobenzaldehyde, iodonaphthaldehyde, iodoanthraldehyde, cyclopropyliodobenzaldehyde, cyclobutyliodobenzaldehyde, cyclopentyliodobenzaldehyde, cyclohexyliodobenzaldehyde, phenyliodobenzaldehyde, naphthyliodobenzaldehyde, adamantyliodobenzaldehyde, norbornyliodobenzaldehyde, lactyliodobenzaldehyde, isopropyliodobenzaldehyde, normal iodobenzaldehyde, bromoiodobenzaldehyde, dimethylaminoiodobenzaldehyde, hydroxyiodobenzaldehyde, dihydroxyiodobenzaldehyde, and trihydroxyiodobenzaldehyde. Iodobenzaldehyde, methyliodobenzaldehyde, dimethyliodobenzaldehyde, and ethyliodobenzaldehyde are more preferable, and iodobenzaldehyde is still more preferable. The aromatic aldehyde compound may have a linear or branched alkyl group of 1 to 4 carbon atoms, a cyano group, a hydroxyl group, halogen, or the like within the range of not deteriorating the effect of the present invention. The aromatic aldehyde compound can be used alone or in combination of two or more kinds.

The aliphatic aldehyde compound is preferably a compound of 3 to 24 carbon atoms. Examples thereof include iodopropanal, iodoisopropanal, iodobutanal, iodoisobutanal, iodo-t-butanal, iodopentanal, iodoisopentanal, iodoneopentanal, iodohexanal, iodoisohexanal, iodooctanal, iododecanal, iodododecanal, iodoundecanal, iodocyclopropanecarboxaldehyde, iodocyclobutanecarboxaldehyde, and iodocyclohexanecarboxaldehyde. Iodoisobutanal, iodo-t-butanal, iodopentanal, iodoisopentanal, iodoneopentanal, iodohexanal, iodoisohexanal, iodooctanal, iododecanal, iodododecanal, iodoundecanal, iodocyclopropanecarboxaldehyde, iodocyclobutanecarboxaldehyde, and iodocyclohexanecarboxaldehyde are more preferable, and iodooctanal, iododecanal, iodododecanal, and iodocyclohexanecarboxaldehyde are still more preferable. The aliphatic aldehyde compound may have a linear or branched alkyl group of 1 to 4 carbon atoms, a cyano group, a hydroxyl group, a halogen atom, or the like within the range of not deteriorating the effect of the present invention. The aliphatic aldehyde compound can be used alone or in combination of two or more kinds.

The acid catalyst used in the above reaction can be arbitrarily selected from publicly known ones and used without particular limitations. An inorganic acid or an organic acid is widely known as such an acid catalyst. Examples thereof include, but not particularly limited to: inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, an organic acid and a solid acid are preferable, and hydrochloric acid and sulfuric acid are more preferable, from the viewpoint of production such as easy availability and handleability. The acid catalyst can be used alone as one kind or in combination of two or more kinds. The amount of the acid catalyst used, which can be arbitrarily set according to the kinds of raw materials and the catalyst, reaction conditions or the like, is not particularly limited and is preferably 0.01 to 100 parts by mass based on 100 parts by mass of the reaction raw materials.

In the above reaction, a reaction solvent may be used. The reaction solvent is not particularly limited as long as the reaction of the aldehyde or the ketone with the biphenol, the bithiophenol, the binaphthol, the bithionaphthol, or the bianthracenediol proceeds. The reaction solvent can be arbitrarily selected from publicly known solvents and used. Examples of the reaction solvent include ethyl acetate, propyl acetate, butyl acetate, 4-butyrolactone, ethylene glycol, propylene glycol, methanol, ethanol, propanol, butanol, tetrahydrofuran, dioxane, ethylene glycol dimethyl ether, ethylene glycol diethyl ether, propylene glycol monomethyl ether, propylene glycol monoethyl ether, propylene glycol monomethyl ether acetate, and mixed solvents thereof. The reaction solvent can be used alone as one kind or in combination of two or more kinds.

The amount of the solvent used, which can be arbitrarily set according to the kinds of raw materials and the catalyst, reaction conditions or the like, is not particularly limited and is preferably 0 to 2000 parts by mass based on 100 parts by mass of the reaction raw materials. The reaction temperature in the above reaction, which can be arbitrarily selected according to the reactivity of the reaction raw materials, is not particularly limited and is usually within the range of 10 to 200° C.

A higher reaction temperature is more preferable from the viewpoint of efficiently obtaining the compound represented by the formula (1) according to the present embodiment. Specifically, the range of 60 to 200° C. is preferable. The reaction method can be arbitrarily selected from publicly known approaches and used without particular limitations. Examples thereof include a method of charging the biphenol, the bithiophenol, the binaphthol, the bithionaphthol, or the bianthracenediol, the aldehyde or the ketone, and the catalyst in one portion, and a method of dropping the biphenol, the bithiophenol, the binaphthol, the bithionaphthol, or the bianthracenediol, and the aldehyde or the ketone in the presence of the catalyst. After the polycondensation reaction terminates, the obtained compound can be isolated according to a routine method without particular limitations. For example, the objective compound can be obtained by adopting a general approach of elevating the temperature of the reaction vessel to 130 to 230° C. in order to remove unreacted raw materials, catalyst, etc. present in the system, and removing volatile portions at a pressure of about 1 to 50 mmHg.

Reaction conditions are not particularly limited and involve, for example, using 1.0 mol to an excess of the biphenol, the bithiophenol, the binaphthol, the bithionaphthol, or the bianthracenediol and 0.001 to 1.0 mol of the acid catalyst based on 1.0 mol of the aldehyde or the ketone, and reacting them at 50 to 1500° C. at normal pressure for about 20 minutes to 100 hours.

The target component can be isolated by a publicly known method after the reaction terminates. An exemplary method can involve concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the compound represented by the above formula (1) which is the objective compound.

[Resin]

The resin according to the present embodiment is a resin derived from the compound represented by the above formula (1) as a monomer. Specific examples of the resin include a resin having a structure represented by the formula (2).

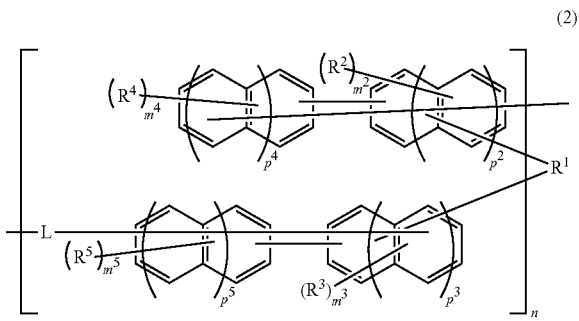

(2)

In the above formula (2), $R^1$ is a 2n-valent group of 1 to 30 carbon atoms; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, or a hydroxyl group, wherein at least one selected from $R^1$ to $R^5$ is a group containing an iodine atom, and at least one of $R^4$ and/or at least one of $R^5$ is one or more kinds selected from a hydroxyl group and a thiol group; L is a linear or branched alkylene group of 1 to 20 carbon atoms or a single bond; $m^2$ and $m^3$ are each independently an integer of 0 to 8; $m^4$ and $m^5$ are each independently an integer of 0 to 9, wherein $m^4$ and $m^5$ are not 0 at the same time; n is an integer of 1 to 4; and $p^2$ to $p^5$ are each independently an integer of 0 to 2.

The resin according to the present embodiment is obtained by reacting the compound represented by the above formula (1) with a compound having crosslinking reactivity.

A publicly known compound can be used as the compound having crosslinking reactivity without particular limitations as long as the compound is capable of oligomerizing or polymerizing the compound represented by the above formula (1). Specific examples thereof include, but not particularly limited to, an aldehyde, a ketone, a carboxylic acid, a carboxylic acid halide, a halogen-containing compound, an amino compound, an imino compound, an isocyanate, and an unsaturated hydrocarbon group-containing compound.

Specific examples of the resin according to the present embodiment include a novolac resin prepared by the condensation reaction or the like of the compound represented by the above formula (1) with an aldehyde as the compound having crosslinking reactivity.

Herein, examples of the aldehyde used in the preparation of the novolac resin from the compound represented by the above formula (1) include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural. Among them, formaldehyde is more preferable from the viewpoint of reactivity. These aldehydes can be used alone as one kind or in combination of two or more kinds. The amount of the aldehyde used is not particularly limited and is preferably 0.2 to 5 mol based on 1 mol of the compound represented by the above formula (1), and more preferably 0.5 to 2 mol.

An acid catalyst may be used in the condensation reaction of the compound represented by the above formula (1) with the aldehyde. The acid catalyst can be arbitrarily selected from publicly known ones and used without particular limitations. An inorganic acid or an organic acid is widely known as such an acid catalyst. Examples thereof include, but not particularly limited to: inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, an organic acid and a solid acid are preferable, and hydrochloric acid and sulfuric acid are more preferable, from the viewpoint of production such as easy availability and handleability. The acid catalyst can be used alone as one kind or in combination of two or more kinds. The amount of the acid catalyst used, which can be arbitrarily set according to the kinds of raw materials and the catalyst, reaction conditions or the like, is not particularly limited and is preferably 0.01 to 100 parts by mass based on 100 parts by mass of the reaction raw materials. However, the aldehyde is not necessarily required for copolymerization reaction with a compound having an unconjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, or limonene.

A reaction solvent may be used in the condensation reaction of the compound represented by the above formula (1) with the aldehyde. The reaction solvent in this polycondensation can be arbitrarily selected from publicly known solvents and used without particular limitations. Examples thereof include water, methanol, ethanol, propanol, butanol, tetrahydrofuran, dioxane, and mixed solvents thereof. The reaction solvent can be used alone as one kind or in combination of two or more kinds.

The amount of the solvent used, which can be arbitrarily set according to the kinds of raw materials and the catalyst, reaction conditions or the like, is not particularly limited and is preferably within the range of 0 to 2000 parts by mass based on 100 parts by mass of the reaction raw materials. The reaction temperature, which can be arbitrarily selected according to the reactivity of the reaction raw materials, is not particularly limited and is usually within the range of 10 to 200° C. The reaction method can be arbitrarily selected from publicly known approaches and used without particular limitations. Examples thereof include a method of charging the compound represented by the above formula (1), the aldehyde, and the catalyst in one portion, and a method of dropping the compound represented by the above formula (1) and the aldehyde in the presence of the catalyst.

After the polycondensation reaction terminates, the obtained compound can be isolated according to a routine method without particular limitations. For example, the novolac resin can be obtained as the target component by adopting a general approach of elevating the temperature of the reaction vessel to 130 to 230° C. in order to remove unreacted raw materials, catalyst, etc. present in the system, and removing volatile portions at a pressure of about 1 to 50 mmHg.

Herein, the resin according to the present embodiment may be a homopolymer of the compound represented by the above formula (1), but may be a copolymer thereof with an additional phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

Alternatively, the resin according to the present embodiment may be a copolymer with a polymerizable monomer other than the above additional phenol. Examples of such a polymerizable monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene. The resin according to the present embodiment may be a binary or higher (e.g., binary to quaternary) copolymer of the compound represented by the above formula (1) with the above phenol, may be a binary or higher (e.g., binary to quaternary) copolymer of the compound represented by the above formula (1) with the above copolymerizable monomer, or may be a ternary or higher (e.g., ternary or quaternary) copolymer of the compound represented by the above formula (1) with the above phenol and the above copolymerizable monomer.

The molecular weight of the resin according to the present embodiment is not particularly limited and is preferably 500 to 30,000 in terms of a polystyrene based weight average molecular weight (Mw), and more preferably 750 to 20,000. When the molecular weight of the resin is 500 or more, film formability tends to be improved. When the molecular weight is 30,000 or less, solubility tends to be improved. The molecular weight distribution (weight average molecular weight Mw/number average molecular weight Mn) of the resin is preferably within the range of 1.2 to 7.0 from the viewpoint of enhancing crosslinking efficiency while suppressing volatile components during baking.

The above molecular weight and molecular weight distribution can be determined by methods described in Examples mentioned later.

[Resist Composition]

The resist composition according to the present embodiment contains the above resist base material and a solvent. The resist composition contains preferably 1 to 80% by mass of the solid component and 20 to 99% by mass of the solvent, more preferably 1 to 50% by mass of the solid component and 50 to 99% by mass of the solvent, still more preferably 2 to 40% by mass of the solid component and 60 to 98% by mass of the solvent, and particularly preferably 2 to 10% by mass of the solid component and 90 to 98% by mass of the solvent.

Herein, the solid component means the summation of solid components such as the resist base material (A), the acid generating agent (C), the acid crosslinking agent (G), the acid diffusion controlling agent (E), and other optional components (F).

The content of the resist base material in the resist composition according to the present embodiment is preferably 50 to 99.4% by mass of the total weight of the solid component, more preferably 55 to 90% by mass, still more preferably 60 to 80% by mass, and particularly preferably 60 to 70% by mass. When the content of the resist base material falls within the above range, high resolution tends to be obtained, and line edge roughness tends to be decreased.

[Solvent]

Examples of the solvent contained in the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents may be used alone or may be used in combination of two or more kinds.

[Acid Generating Agent]

The resist composition of the present embodiment preferably contains one or more acid generating agents (C) generating an acid directly or indirectly by irradiation of any radiation selected from the group consisting of visible light, ultraviolet, excimer laser, electron beam, extreme ultraviolet (EUV), X-ray, and ion beam. The content of the acid generating agent (C) is preferably 0.001 to 49% by mass of the total weight of the solid component, more preferably 1 to 40% by mass, still more preferably 3 to 30% by mass, and particularly preferably 10 to 25% by mass. When the content of the acid generating agent falls within the above range, a pattern profile with high sensitivity and low edge roughness tends to be obtained. In the present embodiment, the acid generation method is not particularly limited as long as an acid is generated in the system. For example, in the case of using excimer laser instead of ultraviolet such as g-ray and i-ray, finer processing is possible, and also in the case of using electron beam, extreme ultraviolet, X-ray or ion beam as a high energy ray, further finer processing is possible.

The acid generating agent (C) is preferably at least one selected from the group consisting of compounds represented by the following formulae (7-1) to (7-8):

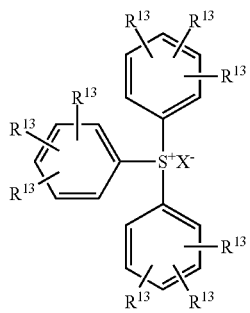

(7-1)

In the formula (7-1), $R^{13}$ may be the same or different, and are each independently a hydrogen atom, a linear, branched or cyclic alkyl group, a linear, branched or cyclic alkoxy group, a hydroxyl group, or a halogen atom; $X^-$ is an alkyl group, an aryl group, a sulfonic acid ion having a halogen substituted alkyl group or a halogen substituted aryl group, or a halide ion.

The compound represented by the above formula (7-1) is preferably at least one selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenylsulfonium-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

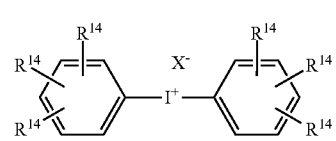

(7-2)

In the formula (7-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.

The compound represented by the above formula (7-2) is preferably at least one selected from the group consisting of bis(4-t-butylphenyl)iodonium trifluoromethanesulfonate, bis(4-t-butylphenyl)iodonium nonafluoro-n-butanesulfonate, bis(4-t-butylphenyl) iodonium perfluoro-n-octanesulfonate, bis(4-t-butylphenyl)iodonium-p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium-p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl) iodonium-p-toluenesulfonate, di(4-trifluoromethylphenyl)iodonium benzenesulfonate, and di(4-trifluoromethylphenyl)iodonium 10-camphersulfonate.

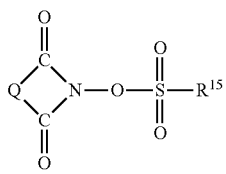
(7-3)

In the formula (7-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (7-3) is preferably at least one selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

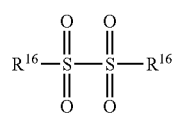
(7-4)

In the formula (7-4), $R^{16}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-4) is preferably at least one selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

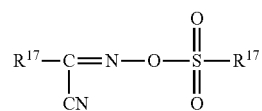
(7-5)

In the formula (7-5), $R^{17}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-5) is preferably at least one selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

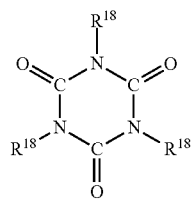
(7-6)

In the formula (7-6), $R^{18}$ may be the same or different, and are each independently a halogenated alkyl group having one or more chlorine atoms and/or bromine atoms. The number of carbon atoms in the halogenated alkyl group is preferably 1 to 5.

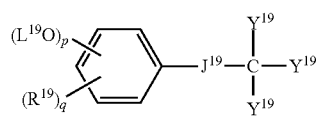
(7-7)

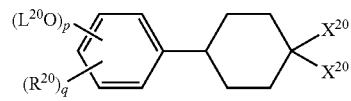
(7-8)

In the above formulae (7-7) and (7-8), $R^{19}$ and $R^{20}$ are each independently an alkyl group of 1 to 3 carbon atoms such as a methyl group, an ethyl group, an n-propyl group, and an isopropyl group; a cycloalkyl group such as a cyclopentyl group and a cyclohexyl group; an alkoxyl group of 1 to 3 carbon atoms such as a methoxy group, an ethoxy group, and a propoxy group; or an aryl group such as a phenyl group, a toluoyl group, and a naphthyl group, and preferably an aryl group of 6 to 10 carbon atoms.

$L^{19}$ and $L^{20}$ are each independently an organic group having a 1,2-naphthoquinonediazide group. Specifically, the organic group having a 1,2-naphthoquinonediazide group is preferably a 1,2-quinonediazidesulfonyl group such as a 1,2-naphthoquinonediazide-4-sulfonyl group, a 1,2-naphthoquinonediazide-5-sulfonyl group, or a 1,2-naphthoquinonediazide-6-sulfonyl group, and more preferably a 1,2-naphthoquinonediazide-4-sulfonyl group or a 1,2-naphthoquinonediazide-5-sulfonyl group.

p is an integer of 1 to 3; q is an integer of 0 to 4; and $1 \leq p+q \leq 5$.

$J^{19}$ is a single bond, a polymethylene group of 1 to 4 carbon atoms, a cycloalkylene group, a phenylene group, a group represented by the following formula (7-7-1), a carbonyl group, an ester group, an amide group, or an ether group.

$Y^{19}$ is a hydrogen atom, an alkyl group, or an aryl group.

$X^{20}$ are each independently a group represented by the following formula (7-8-1):

(7-7-1)

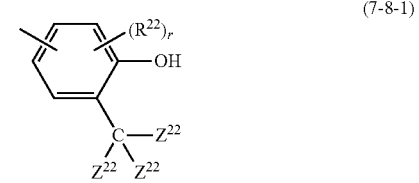
(7-8-1)

In the above formula (7-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the above acid generating agents, an acid generating agent having an aromatic ring is preferable, and an acid generating agent represented by the formula (7-1) or (7-2) is more preferable. An acid generating agent having a sulfonate ion wherein $X^-$ of the formula (7-1) or (7-2) has an aryl group or a halogen-substituted aryl group is still more preferable; an acid generating agent having a sulfonate ion wherein $X^-$ of the formula (7-1) or (7-2) has an aryl group is particularly preferable; and diphenyltrimethylphenylsulfonium-p-toluenesulfonate, triphenylsulfonium-p-toluenesulfonate, triphenylsulfonium trifluoromethanesulfonate, and triphenylsulfonium nonafluoromethanesulfonate are particularly preferable. By using the above acid generating agent, line edge roughness (LER) tends to be able to be reduced.

The acid generating agent (C) may be used alone or in combination of two or more kinds.

[Acid Crosslinking Agent]

The resist composition of the present embodiment preferably contains one or more acid crosslinking agents (G). The acid crosslinking agent (G) is a compound capable of intramolecular or intermolecular crosslinking the compound represented by the formula (1) in the presence of the acid generated from the acid generating agent (C). Examples of such an acid crosslinking agent (G) include a compound having one or more groups (hereinafter, referred to as "crosslinkable group") capable of crosslinking the compound represented by the formula (1).

Specific examples of such a crosslinkable group include (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and an isopropenyl group. As the crosslinkable group of the acid crosslinking agent (G) of the present embodiment, a hydroxyalkyl group and an alkoxyalkyl group are preferable, and an alkoxymethyl group is particularly preferable, from the viewpoint of reactivity.

Examples of the acid crosslinking agent (G) having the above crosslinkable group include (i) a methylol group-containing compound such as a methylol group-containing melamine compound, a methylol group-containing benzoguanamine compound, a methylol group-containing urea compound, a methylol group-containing glycoluril compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluril compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluril compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is usually 5 to 100 mol %, preferably 10 to 60 mol %, and more preferably 15 to 40 mol % based on the total acid functional groups in the compound having a phenolic hydroxyl group, and the alkali soluble resin. When the introduction rate of the crosslinkable group falls within the above range, the crosslinking reaction tends to be sufficient, and a decrease in the film remaining rate, and swelling phenomena and meandering or the like of a pattern tend to be avoided.

In the resist composition of the present embodiment, the acid crosslinking agent (G) is preferably an alkoxyalkylated urea compound or resin thereof, or an alkoxyalkylated glycoluryl compound or resin thereof. Particularly preferable examples of the acid crosslinking agent (G) include compounds represented by the following formulae (8-1) to (8-3) and an alkoxymethylated melamine compound (acid crosslinking agent (G1)).

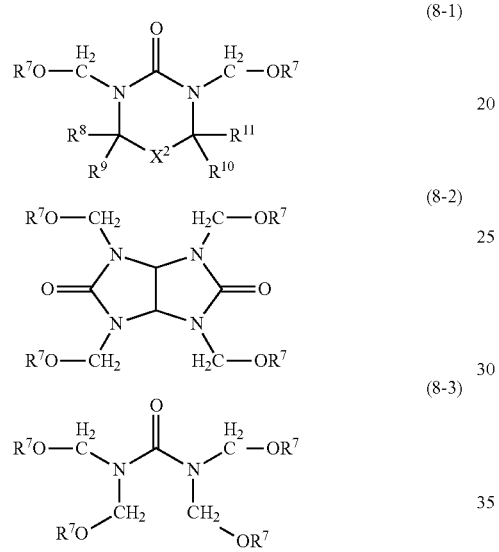

In the above formulae (8-1) to (8-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.

The alkyl group represented by $R^7$ is preferably an alkyl group of 1 to 6 carbon atoms, and more preferably an alkyl group of 1 to 3 carbon atoms. Examples thereof include a methyl group, an ethyl group, and a propyl group. The acyl group represented by $R^7$ is preferably an acyl group of 2 to 6 carbon atoms, and more preferably an acyl group of 2 to 4 carbon atoms. Examples thereof include an acetyl group and a propionyl group. The alkyl group represented by $R^8$ to $R^{11}$ is preferably an alkyl group of 1 to 6 carbon atoms, and more preferably an alkyl group of 1 to 3 carbon atoms. Examples thereof include a methyl group, an ethyl group, and a propyl group. The alkoxyl group represented by $R^8$ to $R^{11}$ is preferably an alkoxyl group of 1 to 6 carbon atoms, and more preferably an alkoxyl group of 1 to 3 carbon atoms. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (8-1) can include compounds represented below:

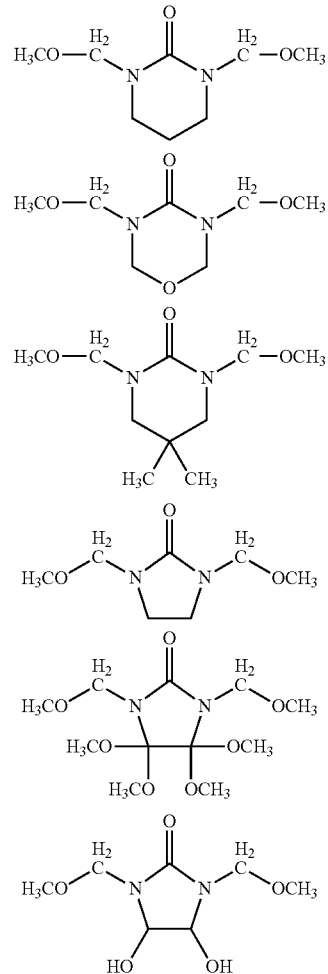

Specific examples of the compound represented by the formula (8-2) include N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among these, N,N,N,N-tetra(methoxymethyl)glycoluryl is particularly preferable.

Specific examples of the compound represented by the formula (8-3) include compounds represented below:

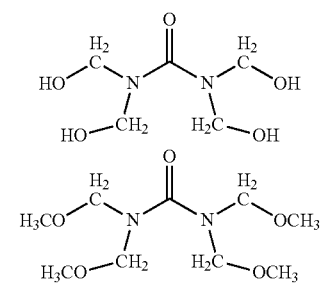

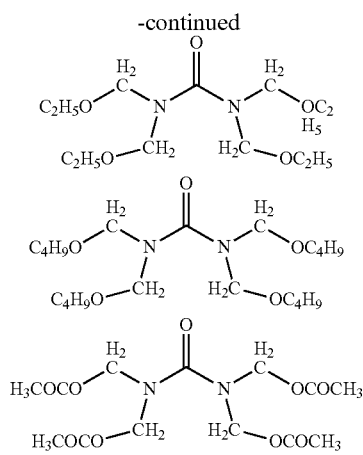

Specific examples of the alkoxymethylated melamine compound include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among these, N,N,N,N,N,N-hexa(methoxymethyl)melamine is particularly preferable.

The above acid crosslinking agent (G1) can be obtained by, for example, conducting a condensation reaction of a urea compound or a glycoluryl compound with formalin to introduce a methylol group, etherifying the product with lower alcohols such as methyl alcohol, ethyl alcohol, propyl alcohol, and butyl alcohol, and then cooling the reaction solution to collect a precipitated compound or resin thereof. As the above acid crosslinking agent (G1), a commercially available product such as CYMEL (trade name, manufactured by MT AquaPolymer) and NIKALAC (manufactured by Sanwa Chemical) may be used.

Other particularly preferable examples of the acid crosslinking agent (G) can include a phenol derivative having 1 to 6 benzene rings within a molecule and two or more hydroxyalkyl groups and/or alkoxyalkyl groups within the molecule, the hydroxyalkyl groups and/or alkoxyalkyl groups being bonded to any of the above benzene rings (acid crosslinking agent (G2)). Among them, a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one or more of the above benzene rings is preferable.

The hydroxyalkyl group bonded to a benzene ring is the one of 1 to 6 carbon atoms such as a hydroxymethyl group, a 2-hydroxyethyl group, and a 2-hydroxy-1-propyl group is preferable. As the alkoxyalkyl group bonded to a benzene ring, the one of 2 to 6 carbon atoms is preferable. Specifically, preferable examples of the group include a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, and a 2-methoxy-1-propyl group.

Among these phenol derivatives, particularly preferable ones are shown below:

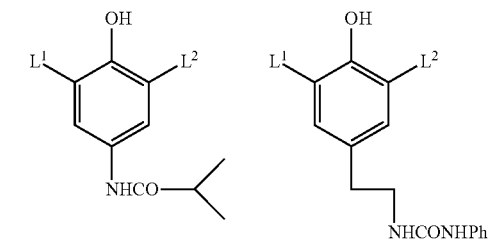

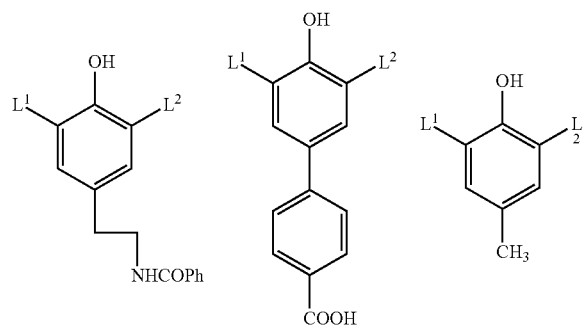

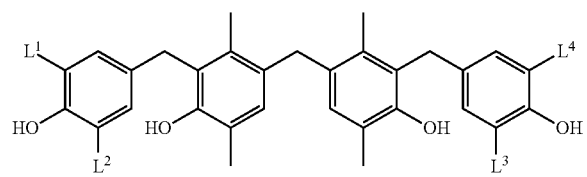

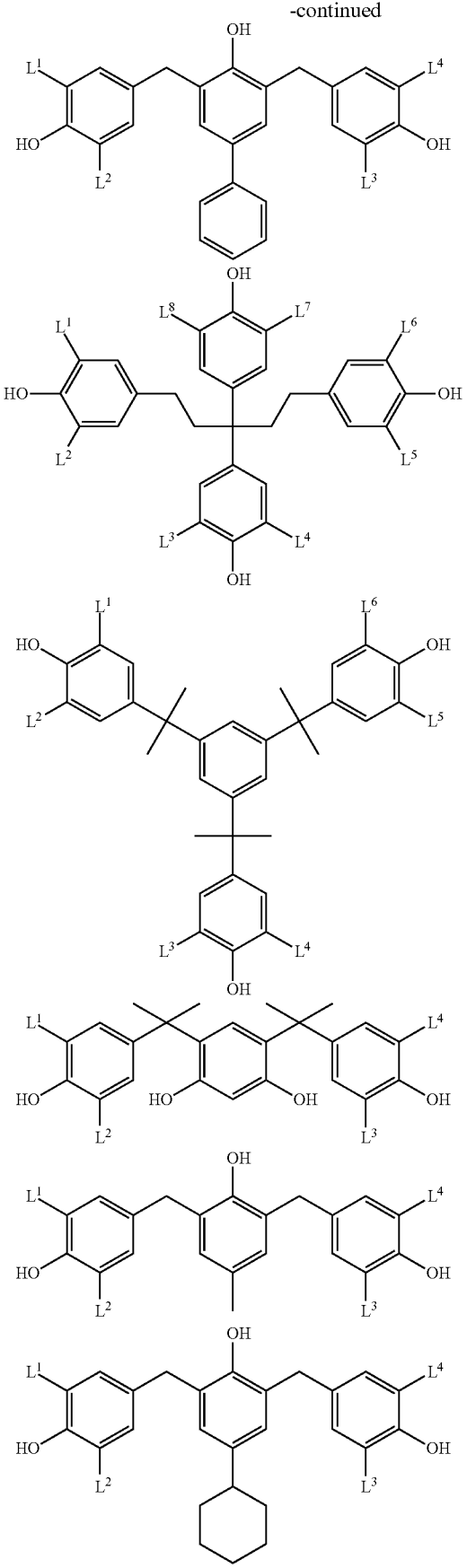

-continued
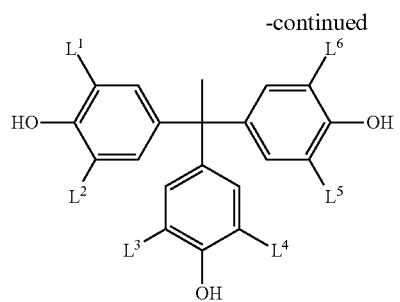
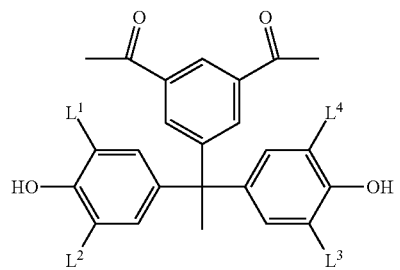
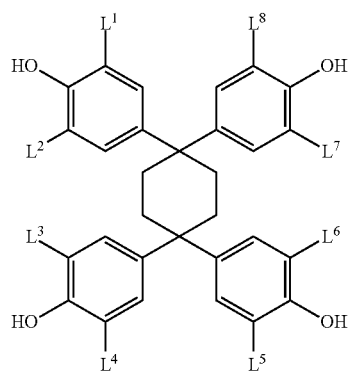
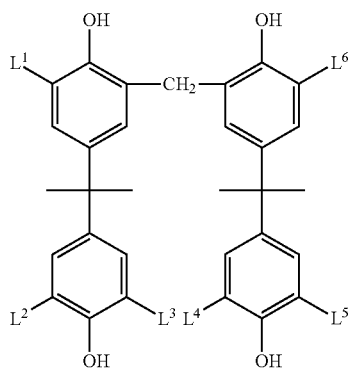
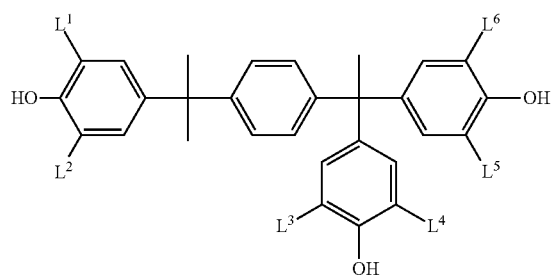

-continued
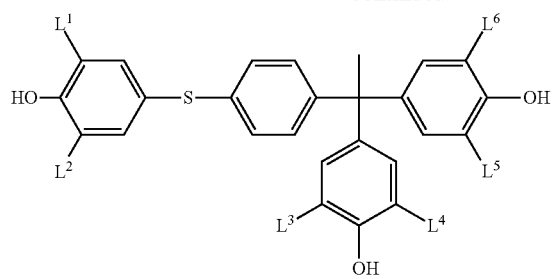
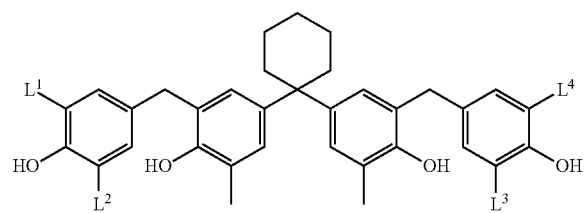
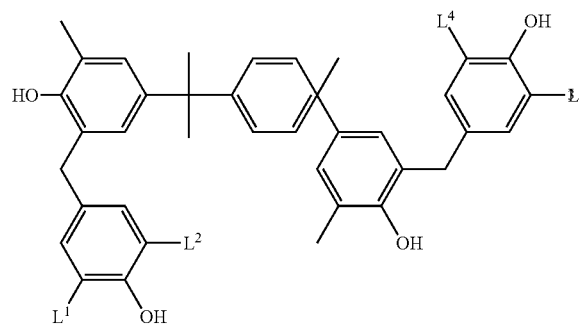
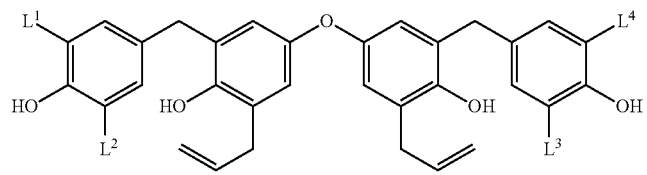
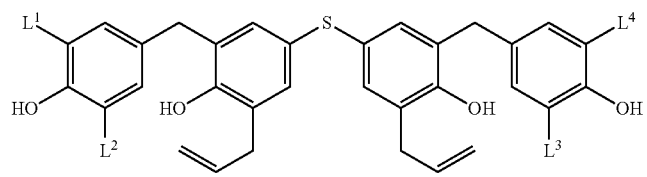
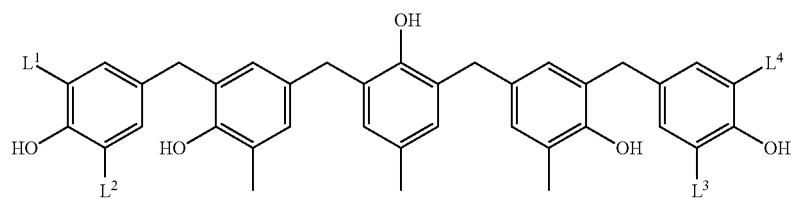

-continued

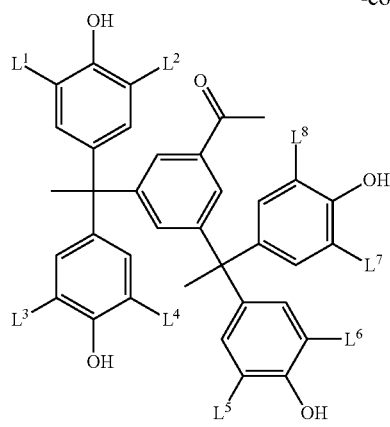 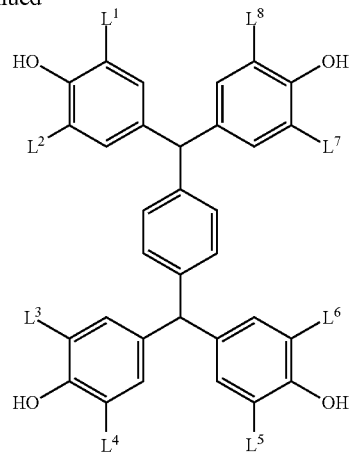

In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the above formulae are a hydrogen atom) with formaldehyde in the presence of a basic catalyst. In this case, the reaction temperature is preferably set to 60° C. or less from the viewpoint of preventing resinification and gelation. Specifically, it can be synthesized according to methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, the reaction temperature is preferably set to 100° C. or less from the viewpoint of preventing resinification and gelation. Specifically, it can be synthesized according to methods described in EP632003A1 or the like.

While the phenol derivative having a hydroxymethyl group and/or an alkoxymethyl group thus synthesized is excellent in stability upon storage, the phenol derivative having an alkoxymethyl group is particularly preferable because it tends to have better stability upon storage. The acid crosslinking agent (G2) may be used alone or may be used in combination of two or more kinds.

Other particularly preferable examples of the acid crosslinking agent (G) can include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation groups (R—COO— group, R—SO$_2$— group or the like, wherein R represents a substituent group selected from the group consisting of a linear hydrocarbon group of 1 to 12 carbon atoms, a cyclic hydrocarbon group of 3 to 12 carbon atoms, an alkoxy group of 1 to 12 carbon atoms, a 1-branched alkyl group of 3 to 12 carbon atoms, and an aromatic hydrocarbon group of 6 to 12 carbon atoms). Examples of a compound having the above α-hydroxyisopropyl group include a substituted or unsubstituted aromatic based compound, a diphenyl compound, a naphthalene compound, a furan compound or the like containing at least one α-hydroxyisopropyl group. Specific examples thereof include a compound represented by the following formula (9-1) (hereinafter, referred to as "benzene based compound (1)"), a compound represented by the following formula (9-2) (hereinafter, referred to as "diphenyl based compound (2)"), a compound represented by the following formula (9-3) (hereinafter, referred to as "naphthalene based compound (3)"), and a compound represented by the following formula (9-4) (hereinafter, referred to as "furan based compound (4)").

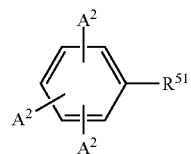

(9-1)

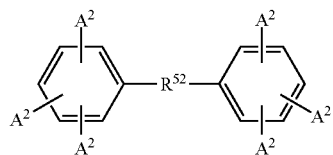

(9-2)

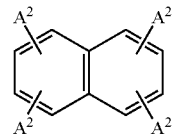

(9-3)

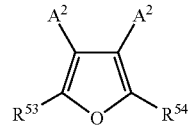

(9-4)

In the above formulae (9-1) to (9-4), each $A^2$ independently represents an α-hydroxyisopropyl group or a hydrogen atom, and at least one $A^2$ is an α-hydroxyisopropyl group. In the formula (9-1), $R^{51}$ represents a hydrogen atom, a hydroxyl group, a linear or branched alkylcarbonyl group of 2 to 6 carbon atoms, or a linear or branched alkoxycarbonyl group of 2 to 6 carbon atoms. Furthermore, in the formula (9-2), $R^{52}$ represents a single bond, a linear or branched alkylene group of 1 to 5 carbon atoms, —O—, —CO—, or —COO—. Also, in the formula (9-4), $R^{53}$ and $R^{54}$ represent a hydrogen atom or a linear or branched alkyl group of 1 to 6 carbon atoms independently from each other.

Specific examples of the benzene based compound (1) include α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) include α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl) biphenyl; α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-bis(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane; α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether; α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) include 1-(α-hydroxyisopropyl) naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α- hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the above furan based compound (4) include 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are still more preferable; and α-hydroxyisopropylbiphenyls having two or more α-hydroxyisopropyl groups and the above naphthalene based compound (3) having two or more α-hydroxyisopropyl groups are particularly preferable.

The above acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

The content of the acid crosslinking agent (G) in the present embodiment is preferably 0.5 to 49% by mass of the total weight of the solid component, more preferably 0.5 to 40% by mass, still more preferably 1 to 30% by mass, and particularly preferably 2 to 20% by mass. When the content of the above acid crosslinking agent (G) is 0.5% by mass or more, the inhibiting effect of the solubility of a resist film in an alkaline developing solution tends to be improved, and a decrease in the film remaining rate, and occurrence of swelling and meandering of a pattern tends to be able to be inhibited. On the other hand, when the content is 49% by mass or less, a decrease in heat resistance as a resist tends to be able to be inhibited.

The content ratio of at least one kind of compound selected from the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

The ratio of the alkoxymethylated melamine compound and/or the compounds represented by the formula (9-1) to the formula (9-3) to all acid crosslinking agent components is preferably 50 to 99% by mass, more preferably 60 to 99% by mass, still more preferably 70 to 98% by mass, and particularly preferably 80 to 97% by mass. By setting the ratio of the alkoxymethylated melamine compound and/or the compounds represented by the formula (9-1) to the formula (9-3) to 50% by mass or more of all acid crosslinking agent components, the resolution tends to be improved. By setting the ratio to 99% by mass or less, the pattern cross section is more likely to have a rectangular shape.

[Acid Diffusion Controlling Agent]

The resist composition of the present embodiment may contain an acid diffusion controlling agent (E). The acid diffusion controlling agent (E) has a function of controlling diffusion of an acid generated from an acid generating agent by radiation irradiation in a resist film to inhibit any unpreferable chemical reaction in an unexposed region or the like. By containing the acid diffusion controlling agent (E), the storage stability of a resist composition tends to be improved. Also, along with the improvement of the resolution, the line width change of a resist pattern due to variation in the post exposure delay time before radiation irradiation and the post exposure delay time after radiation irradiation can be inhibited, and process stability tends to be improved. Such an acid diffusion controlling agent (E) includes a radiation degradable basic compound such as a nitrogen atom-containing basic compound, a basic sulfonium compound, and a basic iodonium compound. The acid diffusion controlling agent (E) can be used alone or can be used in combination of two or more kinds.

Examples of the above acid diffusion controlling agent include a nitrogen-containing organic compound, and a basic compound degradable by exposure. Examples of the above nitrogen-containing organic compound can include a compound represented by the following formula (10):

(10)

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above formula (10), $R^{61}$, $R^{62}$, and $R^{63}$ represent a hydrogen atom, a linear, branched or cyclic alkyl group, an aryl group, or an aralkyl group independently from each other. The above alkyl group, aryl group, or aralkyl group may be unsubstituted or may be substituted with a hydroxyl group or the like. Herein, examples of the above linear, branched or cyclic alkyl group include an alkyl group of 1 to 15 carbon atoms, and preferably 1 to 10 carbon atoms. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include an aryl group of 6 to 12 carbon atoms. Specific examples thereof include a phenyl group, a tolyl group, a xylyl group, a cumenyl group, and a 1-naphthyl group. Furthermore, examples of the above aralkyl group include an aralkyl group of 7 to 19 carbon atoms, and preferably 7 to 13 carbon atoms. Specific examples thereof include a benzyl group, an α-methylbenzyl group, a phenethyl group, and a naphthylmethyl group.

Specific examples of the above nitrogen-containing compound (I) include mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the above nitrogen-containing compound (II) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the above nitrogen-containing compound (III) include polymers of polyethyleneimine, polyarylamine, and N-(2-dimethylaminoethyl)acrylamide.

Specific examples of the above amide group-containing compound include formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the above urea compound include urea, methylurea, 1,1-dimethylurea, 1,3-dimethylurea, 1,1,3,3-tetramethylurea, 1,3-diphenylurea, and tri-n-butylthiourea.

Specific examples of the above nitrogen-containing heterocyclic compound include imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the radiation degradable basic compound can include a sulfonium compound represented by the following formula (11-1):

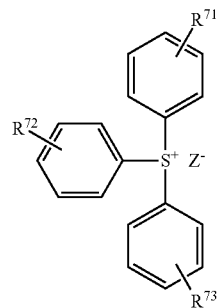
(11-1)

and an iodonium compound represented by the following formula (11-2):

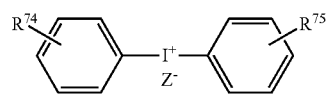
(11-2)

In the above formulae (11-1) and (11-2), $R^{71}$, $R^{72}$, $R^{73}$, $R^{74}$, and $R^{75}$ represent a hydrogen atom, an alkyl group of 1 to 6 carbon atoms, an alkoxyl group of 1 to 6 carbon atoms, a hydroxyl group, or a halogen atom independently from each other. $Z^-$ represents $HO^-$, $R—COO^-$ (wherein R represents an alkyl group of 1 to 6 carbon atoms, an aryl group of 6 to 11 carbon atoms, or an alkaryl group of 7 to 12 carbon atoms), or an anion represented by the following formula (11-3):

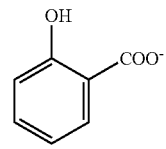
(11-3)

Specific examples of the above radiation degradable basic compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total weight of the solid component, more preferably 0.01 to 10% by mass, still more preferably 0.01 to 5% by mass, and particularly preferably 0.01 to 3% by mass. When the content of the acid diffusion controlling agent falls within the above range, a decrease in resolution, and deterioration of the pattern shape and the dimension fidelity or the like tend to be able to be prevented. Moreover, even though the post exposure delay time from electron beam irradiation to heating after radiation irradiation becomes longer, the shape of the pattern upper layer portion is less likely to be deteriorated. When the content of the acid diffusion controlling agent is 10% by mass or less, a decrease in sensitivity, and developability of the unexposed portion or the like tends to be able to be prevented. By using the acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and process stability tends to be improved.

The resist composition of the present embodiment may contain, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof, within the range of not deteriorating the effect of the present invention.

[Dissolution Promoting Agent]

A low molecular weight dissolution promoting agent is a component having a function of increasing the solubility of a compound represented by the formula (1) in a developing solution to moderately increase the dissolution rate of the compound upon developing, when the solubility of the compound is too low. Examples of the above dissolution promoting agent can include a low molecular weight phenolic compound, for example, bisphenols and tris(hydroxyphenyl)methane. These dissolution promoting agents can be used alone or in mixture of two or more kinds. The content of the dissolution promoting agent, which is arbitrarily adjusted according to the kind of the above compound, is preferably 0 to 49% by mass of the total weight of the solid component, more preferably 0 to 5% by mass, still more preferably 0 to 1% by mass, and particularly preferably 0% by mass.

[Dissolution Controlling Agent]

The dissolution controlling agent is a component having a function of controlling the solubility of the compound represented by the formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

Examples of the dissolution controlling agent include aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or can be used in combination of two or more kinds.

The content of the dissolution controlling agent, which is arbitrarily adjusted according to the kind of the above compound, is preferably 0 to 49% by mass of the total weight of the solid component, more preferably 0 to 5% by mass, still more preferably 0 to 1% by mass, and particularly preferably 0% by mass.

[Sensitizing Agent]

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include benzophenones, biacetyls, pyrenes, phenothiazines, and fluorenes. These sensitizing agents can be used alone or can be used in combination of two or more kinds. The content of the sensitizing agent, which is arbitrarily adjusted according to the kind of the above compound, is preferably 0 to 49% by mass of the total weight of the solid component, more preferably 0 to 5% by mass, still more preferably 0 to 1% by mass, and particularly preferably 0% by mass.

[Surfactant]

The surfactant is a component having a function of improving coatability and striation of the resist composition of the present embodiment, and developability of a resist or the like. Such a surfactant may be any of anionic, cationic, nonionic or amphoteric. A preferable surfactant is a nonionic surfactant. The nonionic surfactant has a good affinity with a solvent used in production of resist compositions, and therefore the effects are more apparent. Specific examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant, which is arbitrarily adjusted according to the kind of the above compound, is preferably 0 to 49% by mass of the total weight of the solid component, more preferably 0 to 5% by mass, still more preferably 0 to 1% by mass, and particularly preferably 0% by mass.

[Organic Carboxylic Acid or Oxo Acid of Phosphor or Derivative Thereof]

For the purpose of prevention of sensitivity deterioration or improvement of a resist pattern shape and post exposure delay stability or the like, the resist composition of the present embodiment may contain, as an optional component, an organic carboxylic acid or an oxo acid of phosphor or derivative thereof. These compounds can be used in combination with the acid diffusion controlling agent, or may be used alone. The organic carboxylic acid is preferably, for example, malonic acid, citric acid, malic acid, succinic acid, benzoic acid, or salicylic acid. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or can be used in combination of two or more kinds. The content of the organic carboxylic acid or the oxo acid of phosphor or derivative thereof, which is arbitrarily adjusted according to the kind of the above compound, is preferably 0 to 49% by mass of the total weight of the solid component, more preferably 0 to 5% by mass, still more preferably 0 to 1% by mass, and particularly preferably 0% by mass.

[Other Additive Agents]

The resist composition of the present embodiment can contain one kind or two kinds or more of other additive agents excluding those mentioned above, within the range of not inhibiting the effect of the present invention, if required. Examples of such an additive agent include a dye, a pigment, and an adhesion aid. For example, the resist composition contains the dye or the pigment, and thereby a latent image of the exposed portion can be visualized and influence of halation upon exposure can be alleviated. The composition contains the adhesion aid, and thereby adhesiveness to a substrate can be improved. Furthermore, examples of other additive agents can include a halation preventing agent, a storage stabilizing agent, a defoaming agent, and a shape improving agent. More specific examples thereof can include 4-hydroxy-4'-methylchalkone.

The total amount of the optional component (F) is preferably 0 to 49% by mass of the total weight of the solid component, more preferably 0 to 5% by mass, still more preferably 0 to 1% by mass, and particularly preferably 0% by mass.

The content of the resist composition of the present embodiment (the resist base material (A)/the acid generating agent (C)/the acid crosslinking agent (G)/the acid diffusion controlling agent (E)/the optional component (F)) is preferably 50 to 99.4/0.001 to 49/0.5 to 49/0.001 to 49/0 to 49 in % by mass based on the solid content, more preferably 55 to 90/1 to 40/0.5 to 40/0.01 to 10/0 to 5, still more preferably 60 to 80/3 to 30/1 to 30/0.01 to 5/0 to 1, and particularly preferably 60 to 70/10 to 25/2 to 20/0.01 to 3/0. The content ratio of each component is selected from each range so that the summation thereof is 100% by mass. In the case of the above content ratio, performance such as sensitivity, resolution, and developability tends to be excellent.

The resist composition of the present embodiment is usually prepared by dissolving each component in a solvent upon use into a homogenous solution, and then if required, filtering through a filter or the like with a pore diameter of about 0.2 μm, for example.

The resist composition of the present embodiment can contain a resin within the range of not inhibiting the effect of the present invention. The resin includes a novolac resin, polyvinyl phenols, polyacrylic acid, polyvinyl alcohol, a styrene-maleic anhydride resin, and a polymer containing acrylic acid, vinyl alcohol, or vinylphenol as a monomeric unit, or derivative thereof. The content of the resin, which is arbitrarily adjusted according to the kind of the resist base material, is preferably 30 parts by mass or less per 100 parts by mass of the resist base material, more preferably 10 parts by mass or less, still more preferably 5 parts by mass or less, and particularly preferably 0 part by mass.

The resist composition of the present embodiment can form an amorphous film by spin coating. The dissolution rate of the amorphous film formed by spin coating with the resist composition of the present embodiment in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film dissolves in a developing solution, and easily produces a resist. When the dissolution rate is 10000 angstrom/sec or less, the resolution tends to be improved. It is presumed that this is because due to the change in the solubility before and after exposure of the compound represented by the above formula (1), contrast at the interface between the unexposed portion being dissolved in a developing solution and the exposed portion not being dissolved in a developing solution is increased. Moreover, when the dissolution rate is 10000 angstrom/sec or less, reduction effects of LER and defect are also found.

The dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and easily produces a resist. When the dissolution rate is 0.0005 angstrom/sec or more, the resolution tends to be improved. It is presumed that this is because the micro surface portion of the compound represented by the above formula (1) dissolves and LER is reduced. Moreover, when the dissolution rate is 0.0005 angstrom/sec or more, reduction effects of defect are also found.

[Resist Pattern Formation Method]

A resist pattern formation method according to the present embodiment includes steps of forming a resist film on a substrate using the above resist composition of the present embodiment, exposing the formed resist film, and developing the exposed resist film, thereby forming a resist pattern. The resist pattern of the present embodiment can also be formed as an upper layer resist in a multilayer process.

In order to form a resist pattern, a resist film is formed by coating a conventionally publicly known substrate with the above resist composition of the present embodiment using a coating means such as spin coating, flow casting coating, and roll coating. Examples of the conventionally publicly known substrate include, but not particularly limited to, a substrate for electronic components, and the one having a predetermined wiring pattern formed thereon. More specific examples include a silicon wafer, a substrate made of a metal such as copper, chromium, iron and aluminum, and a glass substrate. Examples of a wiring pattern material include copper, aluminum, nickel, and gold. Also if required, the above substrate may be a substrate having an inorganic and/or organic film provided thereon. Examples of the inorganic film include an inorganic antireflection film (inorganic BARC). Examples of the organic film include an organic antireflection film (organic BARC). Surface treatment with hexamethylene disilazane or the like may be conducted.

Next, the coated substrate is heated if required. The heating conditions arbitrarily vary according to the compounding composition of the resist composition, or the like, but are preferably in the range of 20 to 250° C., and more preferably 20 to 150° C. By heating the substrate, the adhesiveness of a resist to a substrate tends to be improved. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation. The heating conditions arbitrarily vary according to the compounding composition of the resist composition, or the like, but are preferably in the range of 20 to 250° C., and more preferably 20 to 150° C.

Next, by developing the exposed resist film in a developing solution, a predetermined resist pattern is formed. As the developing solution, a solvent having a solubility parameter (SP value) close to that of the compound of the formula (1) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include dioxane and tetrahydrofuran in addition to the above glycol ether-based solvents.

Examples of the amide-based solvent include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include an aromatic hydrocarbon-based solvent such as toluene and xylene; and an aliphatic hydrocarbon-based solvent such as pentane, hexane, octane, and decane.

The above solvent may be used alone or may be used in mixture of a plurality, or the solvent may be used by mixing the solvent with a solvent other than those described above or water within the range having performance as a developing solution. However, from the viewpoint of obtaining the more apparent effect of the present invention, the water content ratio as the whole developing solution is preferably less than 70% by mass, more preferably less than 50% by mass, still more preferably less than 30% by mass, and further preferably less than 10% by mass. Particularly preferably, the developing solution is substantially moisture free. That is, the content of the organic solvent in the developing solution is preferably 30% by mass or more and 100% by mass or less based on the total amount of the developing solution, more preferably 50% by mass or more and 100% by mass or less, still more preferably 70% by mass or more and 100% by mass or less, further preferably 90% by mass or more and 100% by mass or less, and particularly preferably 95% by mass or more and 100% by mass or less.

Examples of the alkaline aqueous solution include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent tends to improve resist performance such as resolution and roughness of the resist pattern, which is preferable.

The vapor pressure of the developing solution is preferably 5 kPa or less at 20° C., more preferably 3 kPa or less, and still more preferably 2 kPa or less. The evaporation of the developing solution on the substrate or in a developing cup tends to be inhibited by setting the vapor pressure of the developing solution to 5 kPa or less, to improve temperature uniformity within a wafer surface, thereby resulting in improvement in size uniformity within the wafer surface.

Examples of the one having a vapor pressure of 5 kPa or less at 20° C. include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Examples of the one having a vapor pressure of 2 kPa or less at 20° C. include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360, 692, 5,529,881, 5,296,330, 5,436,098, 5,576,143, 5,294,511, and 5,824,451. The surfactant is preferably a nonionic surfactant and more preferably a fluorine-based surfactant or a silicon-based surfactant.

The amount of the surfactant used is usually 0.001 to 5% by mass based on the total amount of the developing solution, preferably 0.005 to 2% by mass, and more preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, for example, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. A rinsing solution containing at least one kind of organic solvent selected from the group consisting of a ketone-based solvent, an ester-based solvent, an alcohol-based solvent and an amide-based solvent is more preferable. A rinsing solution containing an alcohol-based solvent or an ester-based solvent is still more preferable. A rinsing solution containing a monohydric alcohol is further preferable. A rinsing solution containing a monohydric alcohol having 5 or more carbon atoms is particularly preferable. The time of the rinsing step is not particularly limited, but is preferably 10 seconds to 90 seconds.

Herein, examples of the monohydric alcohol used in the rinsing step after development include a linear, branched or cyclic monohydric alcohol. Specific examples include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol. Examples of particularly preferable monohydric alcohol having 5 or more carbon atoms include 1-hexanol, 2-hexanol, 4-methyl-2-pentanol, 1-pentanol, and 3-methyl-1-butanol.

The above rinsing solution may be used alone or may be used in mixture of a plurality, or the rinsing solution may be used by mixing the rinsing solution with an organic solvent other than those described above.

The water content ratio in the rinsing solution is preferably 10% by mass or less, more preferably 5% by mass or less, and still more preferably 3% by mass or less. By setting the water content ratio to 10% by mass or less, better development characteristics tend to be able to be obtained.

The vapor pressure of the rinsing solution is preferably 0.05 kPa or more and 5 kPa or less at 20° C., more preferably 0.1 kPa or more and 5 kPa or less, and still more preferably 0.12 kPa or more and 3 kPa or less. By setting the vapor pressure of the rinsing solution to 0.05 kPa or more and 5 kPa or less, the temperature uniformity in the wafer surface is further enhanced and moreover, swelling due to permeation of the rinsing solution is further inhibited. As a result, the dimensional uniformity in the wafer surface tends to be further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Among them, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate can be obtained by etching. Etching can be conducted using a publicly known method such as dry etching using plasma gas, and wet etching with an alkaline solution, a cupric chloride solution, and a ferric chloride solution or the like.

After forming the resist pattern, plating can also be conducted. Examples of the plating method include copper plating, solder plating, nickel plating, and gold plating.

The remaining resist pattern after etching can be peeled by an organic solvent. Examples of the organic solvent include PGMEA (propylene glycol monomethyl ether acetate), PGME (propylene glycol monomethyl ether), and EL (ethyl lactate). Examples of the peeling method include a dipping method and a spraying method. A wiring substrate having a resist pattern formed thereon may be a multilayer wiring substrate, and may have a small diameter through hole.

The wiring substrate according to the present embodiment can also be formed by a method for forming a resist pattern, then depositing a metal in vacuum, and subsequently dissolving the resist pattern in a solution, i.e., a liftoff method.

EXAMPLES

The present embodiment will be more specifically described with reference to synthesis examples and examples below. However, the present invention is not limited to these examples by any means.

[Measurement Method]

(1) Structure of Compound

The structure of a compound was confirmed by conducting $^1$H-NMR measurement under the following conditions using Advance 60011 spectrometer manufactured by Bruker Corporation.

Frequency: 400 MHz
Solvent: d6-DMSO
Internal standard: TMS
Measurement temperature: 23° C.

(2) Molecular Weight

The molecular weight of a compound was measured using Acquity UPLC/MALDI-Synapt HDMS manufactured by Water Corporation according to LC-MS analysis.

Also, gel permeation chromatography (GPC) analysis was conducted under the following conditions to determine a polystyrene based weight average molecular weight (Mw), a number average molecular weight (Mn), and molecular weight distribution (Mw/Mn).

Apparatus: Shodex GPC-101 model (manufactured by Showa Denko K.K.)
Column: KF-80M×3
Eluent: 1 mL/min THF
Temperature: 40° C.

(3) Thermal Reduction Temperature

"EXSTAR 6000 DSC" apparatus manufactured by SII NanoTechnology Inc. was used. About 5 mg of a sample was placed in an unsealed container made of aluminum, and the temperature was raised to 500° C. at a temperature increase rate of 10° C./min in a nitrogen gas (30 mL/min) stream. In this operation, 10% thermal reduction temperature was measured.

(Synthesis Example 1) Synthesis of BiF-I-1

A container (internal capacity: 200 mL) equipped with a stirrer, a condenser tube, and a burette was prepared. In this container, 30 g (161 mmol) of 4,4-biphenol (reagent manufactured by Tokyo Kasei Kogyo Co., Ltd.), 15 g (65 mmol) of 4-iodobenzaldehyde (reagent manufactured by Tokyo Kasei Kogyo Co., Ltd.), and 100 mL of 4-butyrolactone were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 4.2 g of the objective compound represented by the following formula (BiF-I-1).

As a result of measuring the molecular weight of the obtained compound by the above method, it was 586.

The obtained compound was subjected to NMR measurement under the above measurement conditions. As a result, the following peaks were found, and the compound was confirmed to have a chemical structure represented by the following formula.

δ (ppm) 9.4 (4H, O—H), 6.8-7.8 (18H, Ph-H), 6.2 (1H, C—H)

As a result of thermogravimetry (TG), the 10% thermal reduction temperature of the obtained compound (BiF-I-1) was 300° C. or higher. Therefore, this compound was evaluated as having high heat resistance and being applicable to baking at a high temperature.

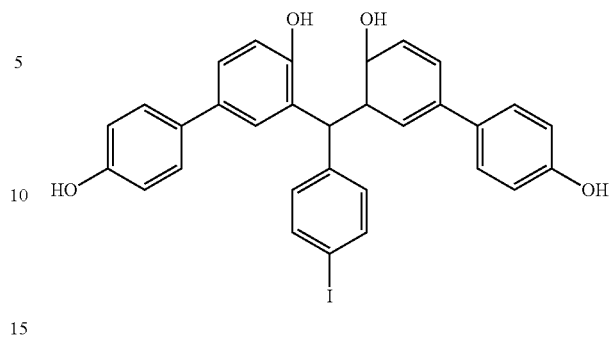

(BiF-I-1)

(Synthesis Example 2) Synthesis of BiF-I-2

A container (internal capacity: 200 mL) equipped with a stirrer, a condenser tube, and a burette was prepared. In this container, 30 g (161 mmol) of 4,4-biphenol (reagent manufactured by Tokyo Kasei Kogyo Co., Ltd.), 15 g (54 mmol) of 5-iodovanillin (reagent manufactured by Tokyo Kasei Kogyo Co., Ltd.), and 100 mL of 4-butyrolactone were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 5.1 g of the objective compound represented by the following formula (BiF-I-2).

As a result of measuring the molecular weight of the obtained compound by the above method, it was 632.

The obtained compound was subjected to NMR measurement under the above measurement conditions. As a result, the following peaks were found, and the compound was confirmed to have a chemical structure represented by the following formula.

δ (ppm) 9.3 (4H, O—H), 6.4-7.3 (16H, Ph-H), 6.1 (1H, C—H)

As a result of thermogravimetry (TG), the 10% thermal reduction temperature of the obtained compound (BiF-I-2) was 300° C. or higher. Therefore, this compound was evaluated as having high heat resistance and being applicable to baking at a high temperature.

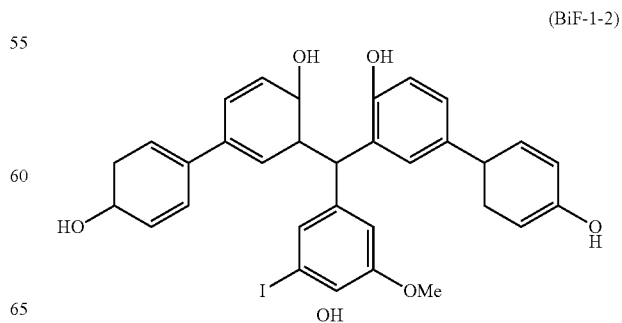

(BiF-1-2)

(Example 3) Synthesis of BiF-I-3

A container (internal capacity: 200 mL) equipped with a stirrer, a condenser tube, and a burette was prepared. In this container, 30 g (161 mmol) of 4,4-biphenol (reagent manufactured by Tokyo Kasei Kogyo Co., Ltd.), 15 g (65 mmol) of 3-iodobenzaldehyde (reagent manufactured by Tokyo Kasei Kogyo Co., Ltd.), and 100 mL of 4-butyrolactone were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 4.2 g of the objective compound represented by the following formula (BiF-I-3).

As a result of measuring the molecular weight of the obtained compound by the above method, it was 586.

The following peaks were found by 400 MHz-$^1$H-NMR, and the compound was confirmed to have a chemical structure of the following formula.

$^1$H-NMR: (d-DMSO, internal standard TMS)

δ (ppm) 9.4 (4H, O—H), 6.5-7.8 (18H, Ph-H), 6.4 (1H, C—H)

As a result of thermogravimetry (TG), the 10% thermal reduction temperature of the obtained compound (BiF-I-3) was 300° C. or higher. Therefore, this compound was evaluated as having high heat resistance and being applicable to baking at a high temperature.

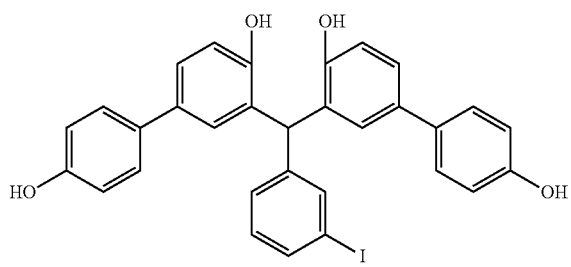

(BiF-I-3)

(Example 4) Synthesis of Resin (BiFR-I-1)

A four necked flask (internal capacity: 1 L) equipped with a Dimroth condenser tube, a thermometer, and a stirring blade and having a detachable bottom was prepared. In this four necked flask, 41.0 g (70 mmol) of BiF-I-1 obtained in Example 1 (manufactured by Mitsubishi Gas Chemical Company, Inc.), 21.0 g (280 mmol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were charged in a nitrogen stream, and reacted for 7 hours while refluxed at 100° C. at normal pressure. Subsequently, 180.0 g of o-xylene (special grade reagent manufactured by Wako Pure Chemical Industries, Ltd.) was added as a diluting solvent to the reaction solution, and it was left at rest, followed by removal of an aqueous phase as a lower phase. Neutralization and washing with water were further performed, and o-xylene was distilled off under reduced pressure to obtain 52.2 g of a brown solid resin (BiFR-I-1).

The obtained resin (BiFR-I-1) had Mn of 1685, Mw of 3120, and Mw/Mn of 1.85.

As a result of thermogravimetry (TG), the 10% thermal reduction temperature of the obtained resin (BiFR-I-1) was 300° C. or higher. Therefore, this compound was evaluated as being applicable to baking at a high temperature.

(Example 5) Synthesis of Resin (BiFR-I-2)

A four necked flask (internal capacity: 1 L) equipped with a Dimroth condenser tube, a thermometer, and a stirring blade and having a detachable bottom was prepared. In this four necked flask, 41.0 g (70 mmol) of BiF-I-1 obtained in Example 1 (manufactured by Mitsubishi Gas Chemical Company, Inc.), 50.9 g (280 mmol) of 4-biphenylaldehyde (manufactured by Mitsubishi Gas Chemical Company, Inc.), 100 mL of anisole (manufactured by Kanto Chemical Co., Inc.), and 10 mL of oxalic acid dihydrate (manufactured by Kanto Chemical Co., Inc.) were charged in a nitrogen stream, and reacted for 7 hours while refluxed at 100° C. at normal pressure. Subsequently, 180.0 g of o-xylene (special grade reagent manufactured by Wako Pure Chemical Industries, Ltd.) was added as a diluting solvent to the reaction solution, and it was left at rest, followed by removal of an aqueous phase as a lower phase. Neutralization and washing with water were further performed, and the solvent of the organic phase and unreacted 4-biphenylaldehyde were distilled off under reduced pressure to obtain 68.2 g of a brown solid resin (BiFR-I-2).

The obtained resin (BiFR-I-2) had Mn of 2080, Mw of 3650, and Mw/Mn of 1.75.

As a result of thermogravimetry (TG), the 10% thermal reduction temperature of the obtained resin (BiFR-I-2) was 300° C. or higher. Therefore, this compound was evaluated as being applicable to baking at a high temperature.

Comparative Example 1

A four necked flask (internal capacity: 10 L) equipped with a Dimroth condenser tube, a thermometer, and a stirring blade and having a detachable bottom was prepared. In this four necked flask, 1.09 kg (7 mol) of 1,5-dimethylnaphthalene (manufactured by Mitsubishi Gas Chemical Company, Inc.), 2.1 kg (28 mol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were charged in a nitrogen stream, and reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction solution, and it was left at rest, followed by removal of an aqueous phase as a lower phase. Neutralization and washing with water were further performed, and ethylbenzene and unreacted 1,5-dimethylnaphthalene were distilled off under reduced pressure to obtain 1.25 kg of a light brown solid dimethylnaphthalene formaldehyde resin.

The obtained dimethylnaphthalene formaldehyde had a molecular weight Mn of 562.

Then, a four necked flask (internal capacity: 0.5 L) equipped with a Dimroth condenser tube, a thermometer, and a stirring blade was prepared. In this four necked flask, 100 g (0.51 mol) of the dimethylnaphthalene formaldehyde resin thus obtained and 0.05 g of p-toluenesulfonic acid were charged under a nitrogen stream. The temperature was raised to 190° C., and it was heated for 2 hours, and then stirred. Subsequently, 52.0 g (0.36 mol) of 1-naphthol was further added thereto. The temperature was further raised to 220° C., and it was reacted for 2 hours. After dilution with a solvent, neutralization and washing with water were performed, and the solvent was removed under reduced pressure to obtain 126.1 g of a blackish brown solid modified resin (CR-1).

The obtained resin (CR-1) had Mn of 885, Mw of 2220, and Mw/Mn of 4.17.

As a result of thermogravimetry (TG), the 10% thermal reduction temperature of the obtained resin (CR-1) was lower than 350° C.

[Evaluation Method]

(1) Test on Safe Solvent Solubility of Compound

The solubility of the compound in cyclohexanone (CHN), propylene glycol monomethyl ether (PGME), and propylene glycol monomethyl ether acetate (PGMEA) was evaluated according to the following standard using the dissolution amount in each solvent. For the measurement of the dissolution amount, the compound was precisely weighed into a test tube at 23° C., and the target solvent was added thereto at a predetermined concentration. Ultrasound was applied for 30 minutes in an ultrasonic cleaning machine. Then, the state of the liquid was visually observed.

Evaluation A: 20% by mass≤dissolution amount

Evaluation B: 10% by mass≤dissolution amount<20.0% by mass

Evaluation C: Dissolution amount<10% by mass (2) Preparation of Resist Composition Each component was prepared according to Table 1 into a homogeneous solution, which was then filtered through a Teflon® membrane filter with a pore diameter of 0.1 µm to prepare a resist composition.

As the acid generating agent (C), the acid crosslinking agent (G), the acid diffusion controlling agent (E), and the solvent, the followings were used:

Acid Generating Agent (C)

P-1: triphenylbenzenesulfonium trifluoromethanesulfonate (Midori Kagaku Co., Ltd.)

Acid Crosslinking Agent (G)

C-1: NIKALAC MW-100LM (Sanwa Chemical Co., Ltd.)

Acid Diffusion Controlling Agent (E)

Q-1: trioctylamine (Tokyo Kasei Kogyo Co., Ltd.)

Solvent

S-1: propylene glycol monomethyl ether (Tokyo Kasei Kogyo Co., Ltd.)

(3) Storage Stability of Resist Composition and Thin Film Formation

Each prepared resist composition was evaluated for its storage stability by the following procedures. The resist composition thus prepared was left at rest at 23° C. for 3 days, and evaluated by visually observing the presence or absence of precipitates. A homogeneous solution without precipitates was evaluated as ○, and a solution having precipitates was evaluated as x.

Also, a clean silicon wafer was spin coated with the resist composition in a homogeneous state, and then prebaked (PB) before exposure in an oven of 110° C. to form a resist film with a thickness of 40 nm. The formed resist film was evaluated as ○ when a good thin film was formed, and evaluated as x when the formed film has defect.

(4) Patterning Evaluation of Resist Composition

Each resist composition was evaluated for patterning by the following procedures. A clean silicon wafer was spin coated with the homogeneous resist composition, and then prebaked (PB) before exposure in an oven of 110° C. to form a resist film with a thickness of 60 nm. The resist film was irradiated with electron beams of 1:1 line and space setting with a 50 nm interval, a 40 nm interval, and a 30 nm interval using an electron beam lithography system (ELS-7500 manufactured by ELIONIX INC.). After electron beam irradiation, it was heated at each predetermined temperature for 90 seconds, and immersed in 2.38% by mass TMAH alkaline developing solution for 60 seconds for development. Subsequently, it was washed with ultrapure water for 30 seconds, and dried to form a negative type resist pattern. The line and space were observed by a scanning electron microscope (S-4800 manufactured by Hitachi High-Technologies Corporation) to evaluate the reactivity of the resist composition by electron beam irradiation.

Solubility in a safe solvent was evaluated by the above method. The results are shown in Table 1.

The storage stability of the obtained composition and thin film formation were evaluated by the above methods. The results are shown in Table 1.

TABLE 1

| | | | | | | Resist performance evaluation Resist composition | | | | | |
|---|---|---|---|---|---|---|---|---|---|---|---|
| | | Safety solvent solubility test | | | Compound of synthesis example | Acid generating agent (C) P-1 [g] | Acid cross-linking agent (G) C-1 [g] | Acid diffusion controlling agent (E) Q-1 [g] | Solvent S-1 [g] | Storage stability | Thin film formation |
| | Compound | CHN | PGME | PGMEA | [g] | | | | | | |
| Example 1 | BiF-I-1 | A | A | A | 1.0 | 0.3 | 0.3 | 0.03 | 50.0 | ○ | ○ |
| Example 2 | BiF-I-2 | A | A | A | 1.0 | 0.3 | 0.3 | 0.03 | 50.0 | ○ | ○ |
| Example 3 | BiF-I-3 | A | A | A | 1.0 | 0.3 | 0.3 | 0.03 | 50.0 | ○ | ○ |
| Example 4 | BiFR-I-1 | B | B | B | 1.0 | 0.3 | 0.3 | 0.03 | 50.0 | ○ | ○ |
| Example 5 | BiFR-I-2 | B | B | B | 1.0 | 0.3 | 0.3 | 0.03 | 50.0 | ○ | ○ |
| Comparative Example 1 | CR-1 | B | B | C | 1.0 | 0.3 | 0.3 | 0.03 | 50.0 | x | x |

As is evident from Table 1, it was able to be confirmed that heat resistance and solubility were good in Examples 1 to 5 whereas Comparative Example 1 was inferior in heat resistance and solubility.

Furthermore, Examples 1 to 5 were confirmed to be free from precipitates and produce good storage stability (evaluation: ○). On the other hand, the resist of Comparative Example 1 manifested precipitates and was confirmed to have poor storage stability (evaluation: x).

Moreover, the resist compositions obtained in Examples 1 to 5 were confirmed to form a good thin film (evaluation: ○). On the other hand, the resist composition obtained in Comparative Example 1 formed a film with defect and was confirmed to form a poor thin film (evaluation: x).

Pattern evaluation was carried out using the resist compositions of Examples 1 to 5 and Comparative Example 1 according to the above method. In Examples 1 to 5, a good resist pattern was obtained by irradiation with electron beams of 1:1 line and space setting with a 50 nm interval. On the other hand, it was confirmed that a good resist pattern was not obtained in Comparative Example 1.

As seen in the above results, the resist base material of the present embodiment has high heat resistance and solubility in a safe solvent, has good storage stability, forms a good thin film, and can impart a good shape to a resist pattern, as compared with a resist base material containing the comparative compound (CR-1).

As long as the above configuration of the present invention is met, resist base materials other than those described in examples also exhibit the same effects.

This application is based on Japanese Patent Application No. 2015-069991 filed with JPO on Mar. 30, 2015, the entire contents of which are hereby incorporated by reference.

The resist base material of the present invention has high heat resistance, has high solubility in a safe solvent, is excellent in storage stability, enables the formation of a good thin film, and imparts a good shape to a resist pattern. Thus, the present invention has industrial applicability in the field of semiconductors, the field of displays, photomasks, thin film magnetic heads, compound semiconductors, research and development, and the like in which a resist composition such as an acid amplification type non-polymer based resist material is used.

The invention claimed is:

1. A resist composition comprising:
   a solvent; and
   a resist base material comprising a compound represented by the following formula (1) and/or a resin derived from the compound as a monomer

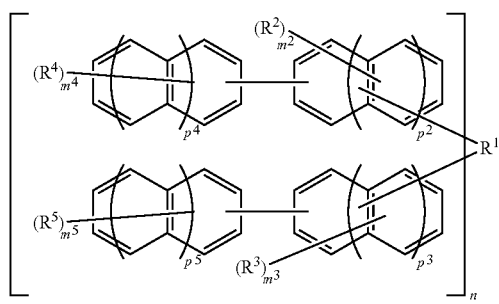

wherein $R^1$ is a 2n-valent group of 1 to 30 carbon atoms; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, or a hydroxyl group, wherein at least one selected from $R^1$ to $R^5$ is a group containing an iodine atom, and at least one of $R^4$ and/or at least one of $R^5$ is selected from a hydroxyl group and a thiol group; $m^2$ and $m^3$ are each independently an integer of 0 to 8; $m^4$ and $m^5$ are each independently an integer of 0 to 9, wherein $m^4$ and $m^5$ are not 0 at the same time; n is an integer of 1 to 4; and $p^2$ to $p^5$ are each independently an integer of 0 to 2.

2. The resist composition according to claim 1, wherein at least one of $R^2$ and/or at least one of $R^3$ is selected from a hydroxyl group and a thiol group.

3. The resist composition according to claim 1, wherein the compound represented by the formula (1) is a compound represented by the following formula (1a):

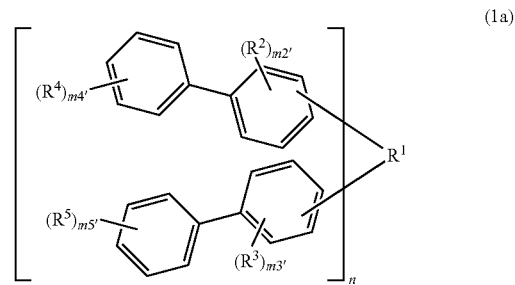

wherein $R^1$ to $R^5$ and n are as defined in claim 1; $m^{2'}$ and $m^{3'}$ are each independently an integer of 0 to 4; and $m^{4'}$ and $m^{5'}$ are each independently an integer of 0 to 5, wherein $m^{4'}$ and $m^{5'}$ are not 0 at the same time.

4. The resist composition according to claim 3, wherein the compound represented by the formula (1a) is a compound represented by the following formula (1b):

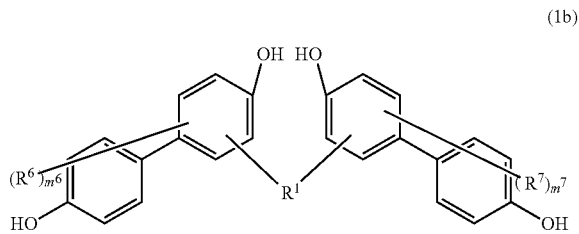

wherein $R^1$ is a 2n-valent group of 1 to 30 carbon atoms; $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, or a thiol group, wherein at least one selected from $R^1$, $R^6$, and $R^7$ is a group containing an iodine atom; and $m^6$ and $m^7$ are each independently an integer of 0 to 7.

5. The resist composition according to claim 4, wherein the compound represented by the formula (1b) is a compound represented by the following formula (1c):

(1c)

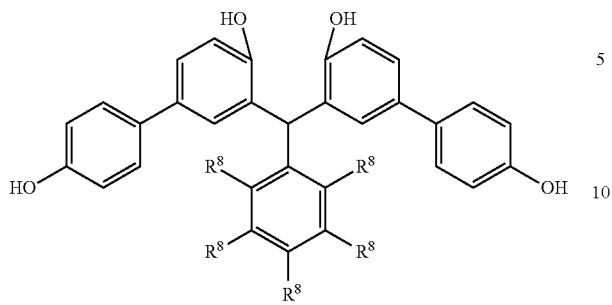

wherein R⁸ are each independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group, wherein at least one of $R^8$ is a group containing an iodine atom.

6. The resist composition according to claim 5, wherein the compound represented by the formula (1c) is a compound represented by the following formula (1d):

(1d)

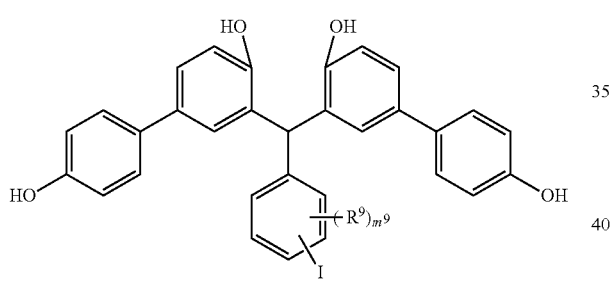

wherein $R^9$ are each independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkenyl group of 2 to 10 carbon atoms, an alkoxy group of 1 to 30 carbon atoms, a thiol group, or a hydroxyl group; and $m^9$ is an integer of 0 to 4.

7. The resist composition according to claim 1, wherein the resin is a resin obtained by reacting the compound represented by the formula (1) with a compound having crosslinking reactivity.

8. The resist composition according to claim 7, wherein the compound having crosslinking reactivity is an aldehyde, a ketone, a carboxylic acid, a carboxylic acid halide, a halogen-containing compound, an amino compound, an imino compound, an isocyanate, or an unsaturated hydrocarbon group-containing compound.

9. The resist composition according to claim 1, wherein the resin has a structure represented by the following formula (2):

(2)

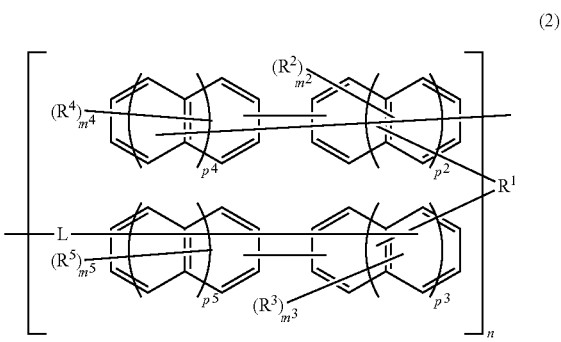

wherein $R^1$ is a 2n-valent group of 1 to 30 carbon atoms; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, or a hydroxyl group, wherein at least one selected from $R^1$ to $R^5$ is a group containing an iodine atom, and at least one of $R^4$ and/or at least one of $R^5$ is selected from a hydroxyl group and a thiol group; L is a linear or branched alkylene group of 1 to 20 carbon atoms or a single bond; $m^2$ and $m^3$ are each independently an integer of 0 to 8; $m^4$ and $m^5$ are each independently an integer of 0 to 9, wherein $m^4$ and $m^5$ are not 0 at the same time; n is an integer of 1 to 4; and $p^2$ to $p^5$ are each independently an integer of 0 to 2.

10. The resist composition according to claim 1, further comprising an acid generating agent.

11. The resist composition according to claim 10, further comprising an acid crosslinking agent.

12. A method for forming a resist pattern, comprising the steps of:
coating a substrate with the resist composition according to claim 10, thereby forming a resist film;
exposing the formed resist film to radiation; and
developing the exposed resist film to form the resist pattern.

13. The resist composition according to claim 1, further comprising an acid crosslinking agent.

14. A method for forming a resist pattern, comprising the steps of:
coating a substrate with the resist composition according to claim 1, thereby forming a resist film;
exposing the formed resist film to radiation; and
developing the exposed resist film to form the resist pattern.

* * * * *

UNITED STATES PATENT AND TRADEMARK OFFICE
CERTIFICATE OF CORRECTION

PATENT NO. : 10,642,156 B2
APPLICATION NO. : 15/562841
DATED : May 5, 2020
INVENTOR(S) : Takumi Toida et al.

Page 1 of 1

It is certified that error appears in the above-identified patent and that said Letters Patent is hereby corrected as shown below:

Column 80, Lines (46-54):

In Claim 4, delete " 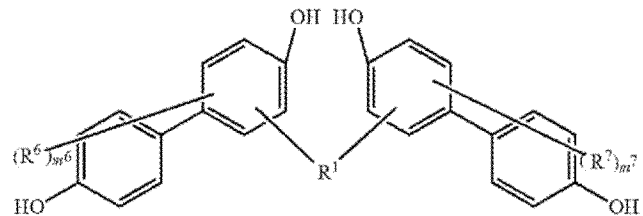 " and insert

-- 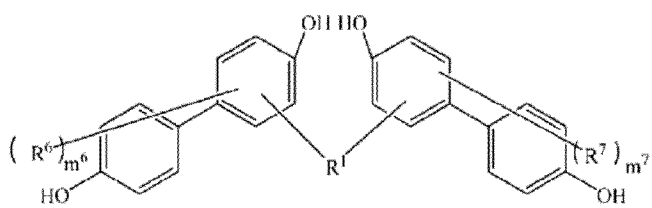 --, therefor.

Signed and Sealed this
Tenth Day of November, 2020

Andrei Iancu
*Director of the United States Patent and Trademark Office*